US008394832B2

(12) United States Patent
Xu et al.

(10) Patent No.: US 8,394,832 B2
(45) Date of Patent: Mar. 12, 2013

(54) METHODS AND COMPOSITIONS USING IMMUNOMODULATORY COMPOUNDS FOR THE TREATMENT OF IMMUNODEFICIENCY DISORDERS

(75) Inventors: Weiming Xu, San Diego, CA (US); Laura G. Corral, San Diego, CA (US)

(73) Assignee: Celgene Corporation, Summit, NJ (US)

( * ) Notice: Subject to any disclaimer, the term of this patent is extended or adjusted under 35 U.S.C. 154(b) by 838 days.

(21) Appl. No.: 11/289,723

(22) Filed: Nov. 30, 2005

(65) Prior Publication Data
US 2006/0188475 A1      Aug. 24, 2006

Related U.S. Application Data

(60) Provisional application No. 60/631,870, filed on Dec. 1, 2004.

(51) Int. Cl.
*A61K 31/4015* (2006.01)
*A61K 31/403* (2006.01)
(52) U.S. Cl. ....................................................... 514/323
(58) Field of Classification Search .................... 514/323
See application file for complete search history.

(56) References Cited

U.S. PATENT DOCUMENTS

| 5,635,517 | A  | * | 6/1997  | Muller et al. ................ 514/323 |
| 6,316,471 | B1 |   | 11/2001 | Muller et al. ................ 514/323 |
| 8,153,659 | B2 | * | 4/2012  | Ruchelman et al. ......... 514/323 |
| 2003/0096841 | A1 | * | 5/2003  | Robarge et al. ............. 514/323 |
| 2004/0014039 | A1 | * | 1/2004  | Rosen et al. ..................... 435/6 |
| 2004/0044034 | A1 | * | 3/2004  | Hayashi et al. .............. 514/314 |

FOREIGN PATENT DOCUMENTS

WO   WO 2004/004364 A1   5/2004
WO   WO 2005/091991 A2  10/2005

OTHER PUBLICATIONS

Zeldis, et al.; "Potential New Therapeutics for Waldenstrom's Macroglobulinemia"; Apr. 2003; Seminars in Oncology; 30(2): 275-281.*
Groux, et al.; "Forum on interleukin-10: The complex role of interleukin-10 in autoimmunity"; 2003 Journal of Autoimmunity; 20: 281-185.*
Tong, et al.; "CD40 and the Effect of Anti-CD40-Binding on Human Multiple Myeloma Clonogenicity"; 1996; Leukemia and Lymphoma; 21(1): 1-8.*
Dredge et al.; "Protective Antitumor Immunity Induced by a Costimulatory Thalidomide Analog in Conjunction with Whole Tumor Cell Vaccination Is Mediated by Increased Th1-Type Immunity" 2002; The Journal of Immunology; 168: 4914-4919.*
Cataldo et al.; "Plasma cytokine profiles in patients with celiac disease and selective IgA deficiency"; Aug. 2003; Pediatric Allergy and Immunology; 14: 320-324.*
Aukrust et al.; "Decreased vitamin a levels in common variable immunodeficiency: vitamin A supplementation in vivo enhances immunoglobulin production and downregulates inflammatory responses"; 2000; European Journal of Clinical Investigation; 30: 252-259.*
Punnonen et al.; "Soluble and Membrane-bound Forms of Signaling Lymphocytic Activation Molecule (SLAM) induce Proliferation and If Synthesis by Activated Human B Lymphocytes"; 1997; J. Exp. Med.; 185(6): 993-1004.*
Kaneko et al.; IgA subclass and IgA deficiency.; 2009; Nihon Rinsho Meneki Gakkai Kaishi; 32(3): 142-8; PubMed abstract; PMID: 19564710.*
Smith et al.; Increased Prevalence of Immunoglobulin A Deficiency in Patients with the Chromosome 22 q11.2 Deletion Syndrome (DiGeorge Syndrome/Velocardiofacial Syndrome); 1998; Clinical and Diagnostic Laboratory Immunology; 5(3): 415-417.*
Siwinska-Golebiowska et al.; "Immunological confirmation of allergy in children with hypoimmunoglobulinemia"; 2003; Md. Wieku Rozwoj.; 7(2): 279-87.*
English Translation of Siwinska-Golebiowska et al.; "Immunological confirmation of allergy in children with hypoimmunoglobulinemia"; 2003; Md. Wieku Rozwoj.; 7(2): 279-87.*
Haslett et al., *Journal of Infectious Diseases*, 187(6): 946-955 (2003).
LeBlanc et al., *Blood*, 103(5): 1787-1790 (2004).
Summary of Cowling et al., *Annals of the Rheumatic Diseases*, 39: 545-549 (1980).
Kugler, R. N., "Autoimmune Kidney Disease" (2003), obtained from http://rarediseases.about.com/cs/iganephropathy/a/042002.htm.

* cited by examiner

*Primary Examiner* — Timothy Thomas
(74) *Attorney, Agent, or Firm* — Jones Day

(57) ABSTRACT

Methods of treating, preventing and/or managing an immunodeficiency disease or disorder are disclosed. Specific methods encompass the administration of an immunomodulatory compound alone or in combination with a second active agent. Methods of boosting humoral immunity are also disclosed.

10 Claims, 19 Drawing Sheets

FIG. 1. 1,3-dioxo-(2,6-dioxopiperidin-3-yl)-4-aminoisoindoline upregulates CD80 expression on normal B cells treated with CD40L and IL-4. Flow cytometric analysis showing that the mean intensity of CD80 is increased by 1,3-dioxo-(2,6-dioxopiperidin-3-yl)-4-aminoisoindoline (A) and the number of B cells expressing CD80 is also increased by 1,3-dioxo-(2,6-dioxopiperidin-3-yl)-4-aminoisoindoline (B).

A. CD40 expression
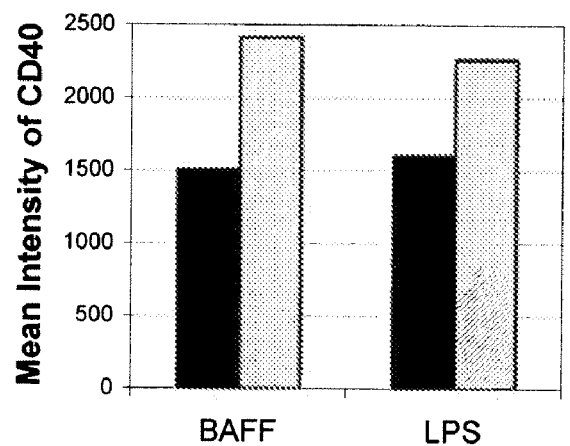
B. HLA-DR expression
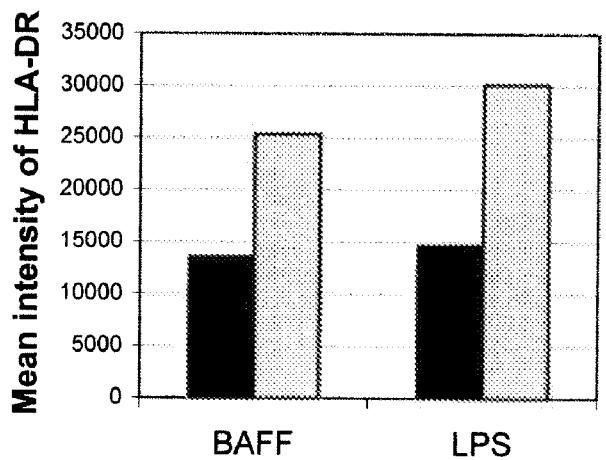
FIG. 2. Flow cytometric analysis showed that 1,3-dioxo-(2,6-dioxopiperidin-3-yl)-4-aminoisoindoline upregulates the expression of CD40 (A) and HLA-DR (B) on normal B cells treated with either BAFF or LPS. Data obtained from DMSO are denoted as black box, and data obtained from 1,3-dioxo-(2,6-dioxopiperidin-3-yl)-4-aminoisoindoline are denoted as lined box.

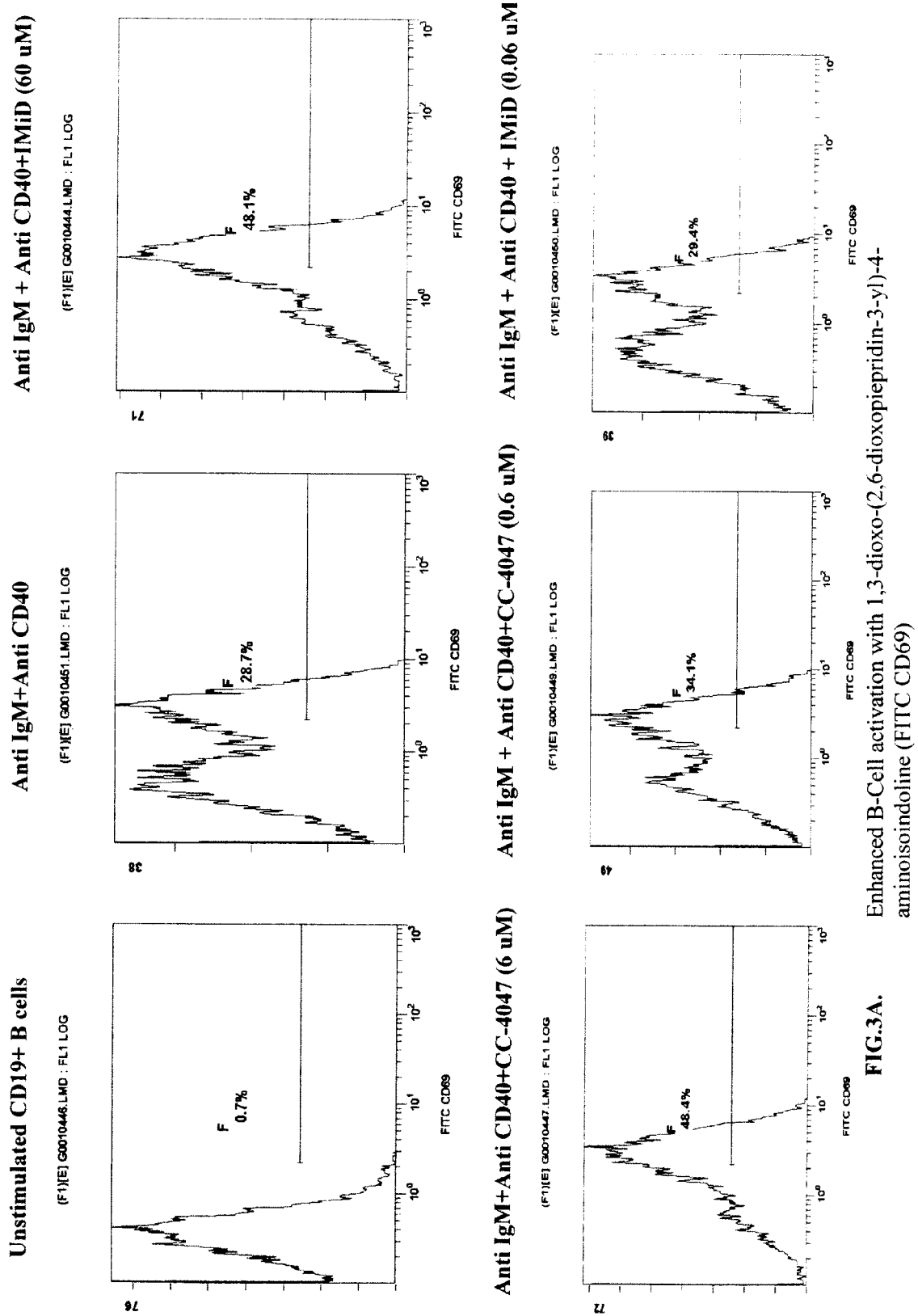
FIG.3A. Enhanced B-Cell activation with 1,3-dioxo-(2,6-dioxopiepridin-3-yl)-4-aminoisoindoline (FITC CD69)

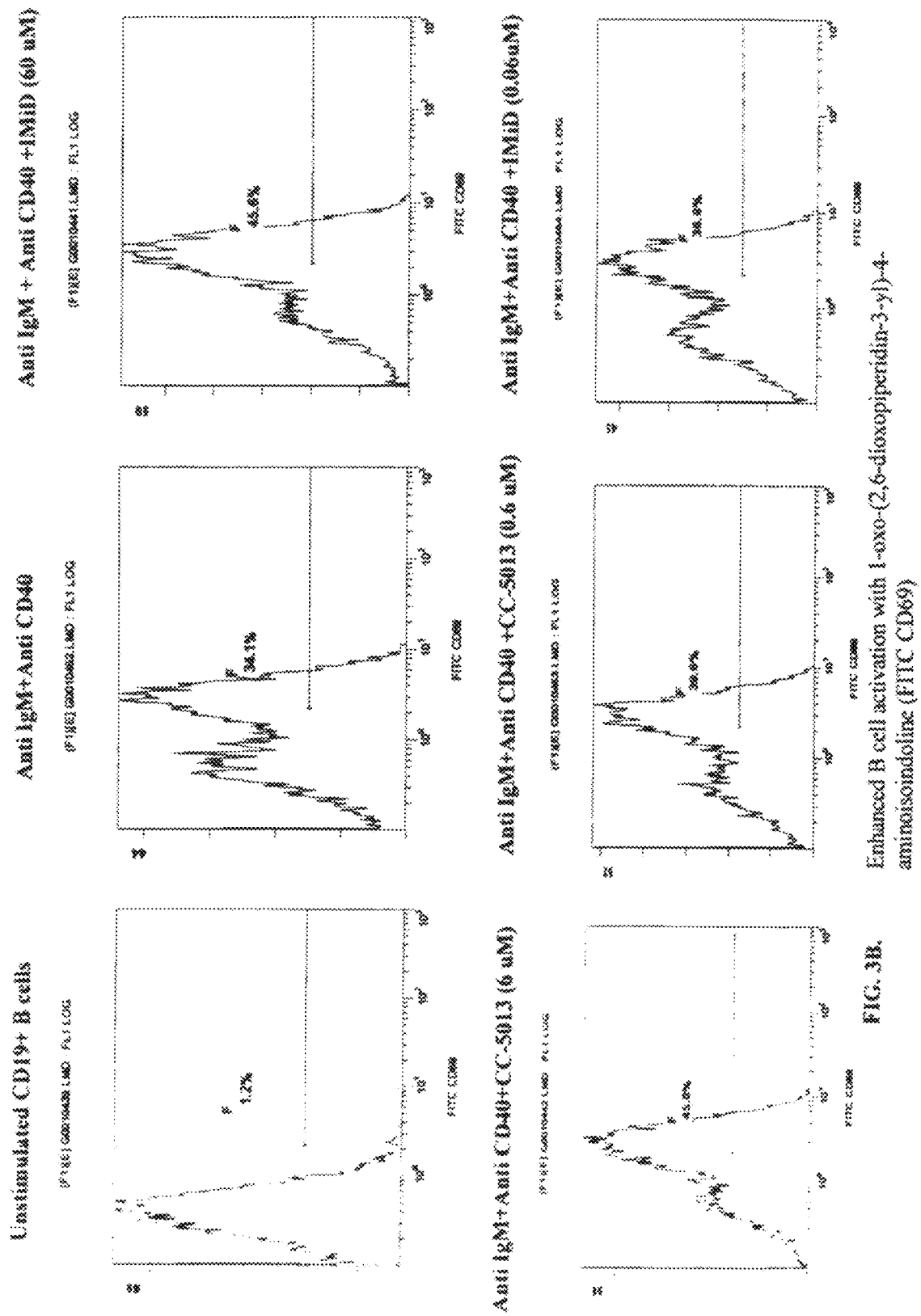

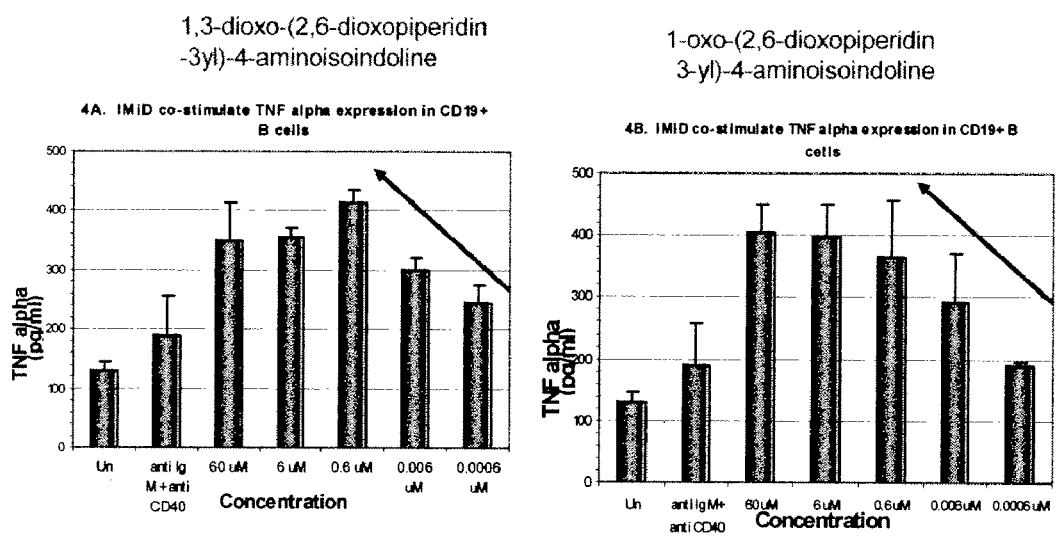
FIG. 4. TNF-α ELISA shows IMiDs significantly enhance TNF-α production in B cells treated with 1,3-dioxo-(2,6-dioxopiperidin-3-yl)-4-aminoisoindoline (A) and 1-oxo-(2,6-dioxopiperidin-3-yl)-4-aminoisoindoline (B) for 72 hours in presence of anti human IgM, anti human CD40 and recombinant human IL-4.

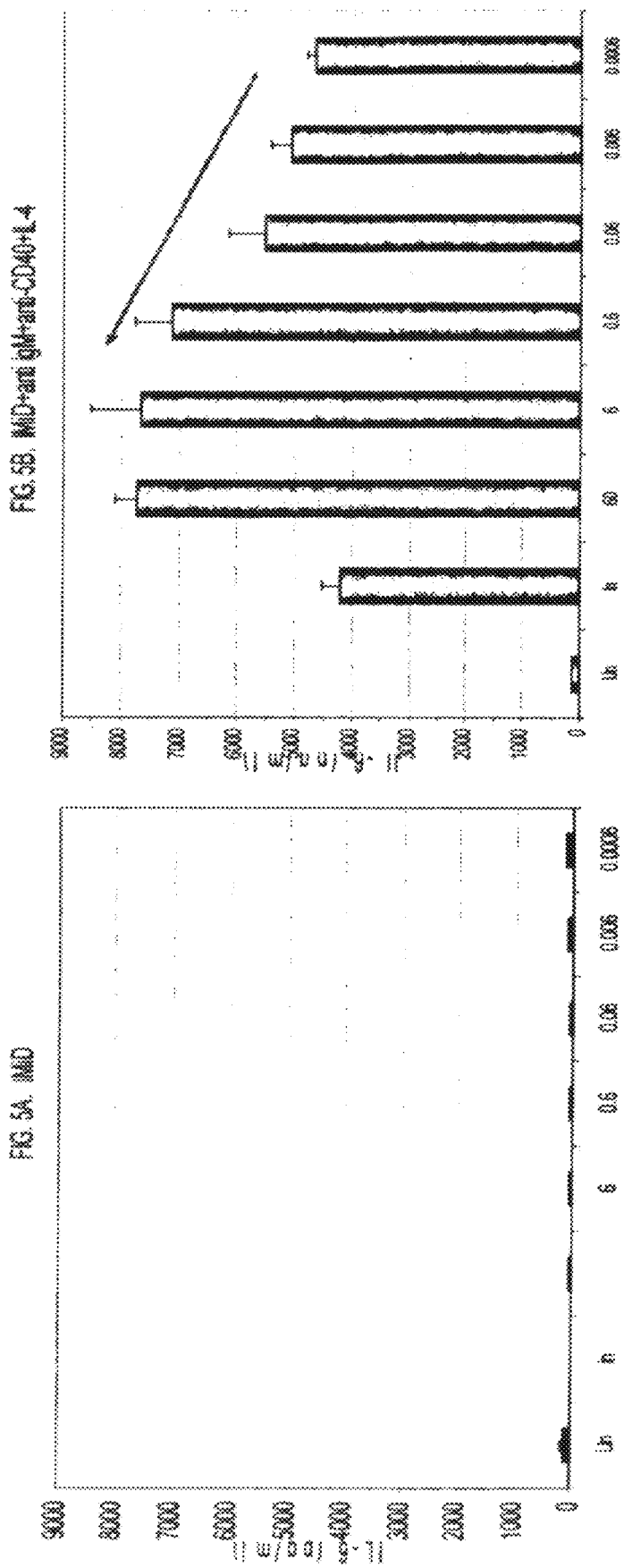
FIG. 5. Cytokine analysis (Luminex) shows that 1,3-dioxo-(2,6-dioxopiperidin-3-yl)-4-aminoisoindoline increases IL-6 expression at dose dependent manner in presence of anti human IgM, anti human CD40 and recombinant human IL-4 (B), but shows a minimal effect in the absence of other stimuli (A).

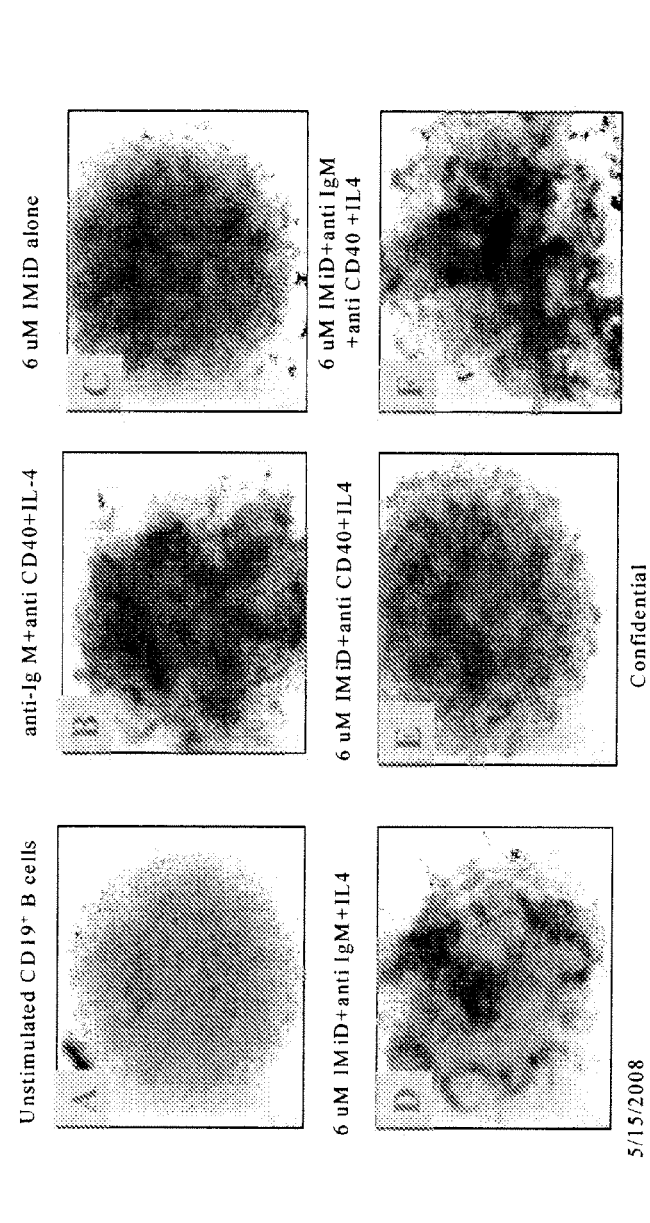

FIG. 6. Morphology of entire cell culture at 96 well plate (U bottom, phase contrast microscopy) in 1,3-dioxo-(2,6-dioxopiperidin-3-yl)-4-aminoisoindoline treated normal B cells in the presence of anti IgM, anti CD40 and IL-4: (A) Unstimulated CD19⁺ B cells; (B) Stimulated CD19⁺ B cells (anti IgM, anti CD40 and IL-4) showed a spiky shape on the edge of entire culture; (C) CD19⁺ B cells with CC-4047 alone showed increased density and slight change on the edge; (D) 1,3-dioxo-(2,6-dioxopiperidin-3-yl)-4-aminoisoindoline treated B cells in the presence of anti IgM and IL-4; (E) 1,3-dioxo-(2,6-dioxopiperidin-3-yl)-4-aminoisoindoline treated B cells in the presence of anti CD40 and IL-4; and (F) 1,3-dioxo-(2,6-dioxopiperidin-3-yl)-4-aminoisoindoline treated normal B cells in the presence of anti IgM, anti CD40 and IL-4 showed more obvious spiky shape than stimulated CD19⁺ B cells.

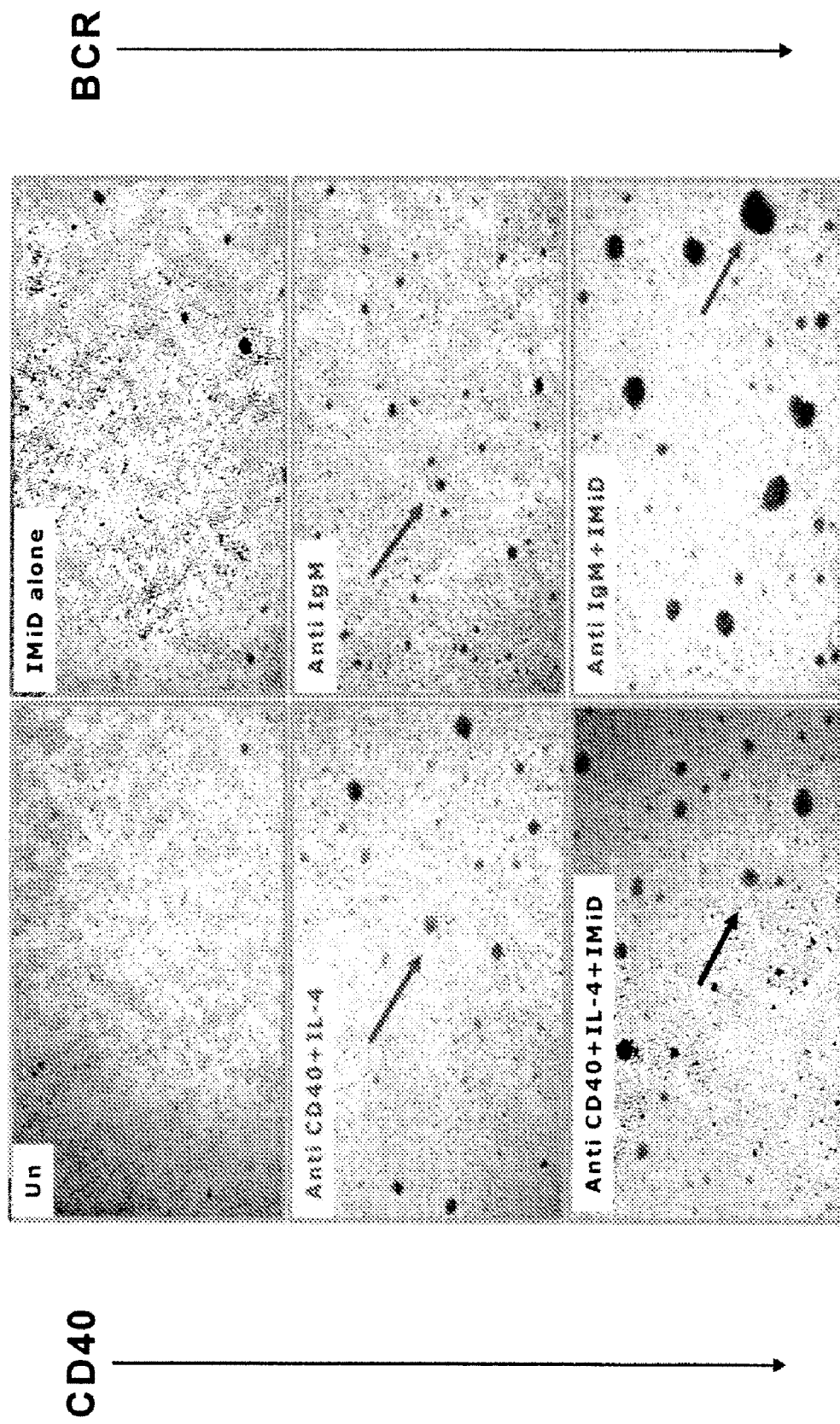
FIG. 7B. Comparison of Morphological Changes in Stimulated B Cells

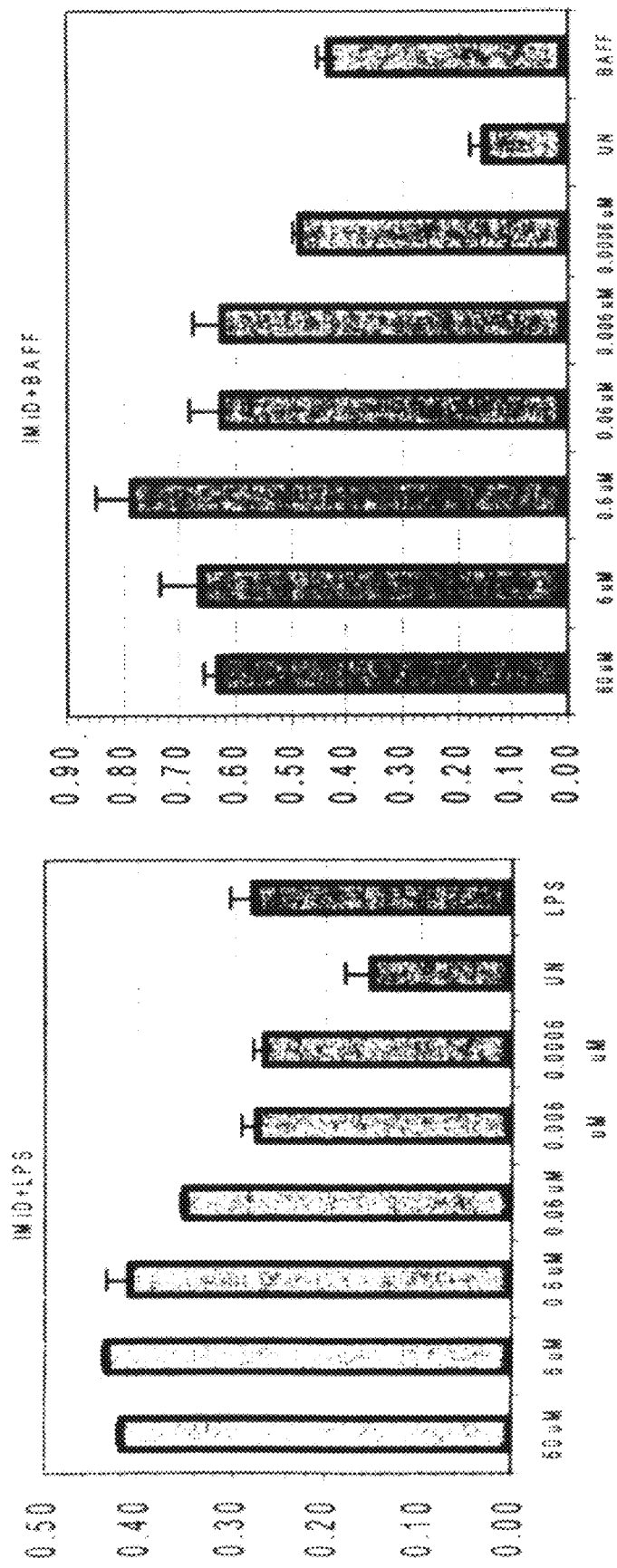

FIG. 7. B cell proliferation (BrdU ELISA) in 1,3-dioxo-(2,6-dioxopiperidin-3-yl)-4-aminoisoindoline or 1-oxo-(2,6-dioxopiperidin-3-yl)-4-aminoisoindoline treated normal B cells in the presence of anti IgM. (A) 1,3-dioxo-(2,6-dioxopiperidin-3-yl)-4-aminoisoindoline or 1-oxo-(2,6-dioxopiperidin-3-yl)-4-aminoisoindoline treated CD19+ B cells, with or without IgM. (B) Comparison of morphological changes in 1,3-dioxo-(2,6-dioxopiperidin-3-yl)-4-aminoisoindoline treated B cells, along with other stimuli. (C) Effect of 1,3-dioxo-(2,6-dioxopiperidin-3-yl)-4-aminoisoindoline on LPS and BAFF stimulated cell proliferation.

1,3-dioxo-(2,6-dioxopiperidin-3-yl)-4-aminoisoindoline increases TLR9 expression in presence of B cells stimulation 1,3-dioxo-(2,6-dioxopiperidin-3-yl)-4-aminoisoindoline with anti CD40 and IL-4

FIG. 8C.

1,3-dioxo-(2,6-dioxopiperidin-3-yl)-4-aminoisoindoline with anti IgM

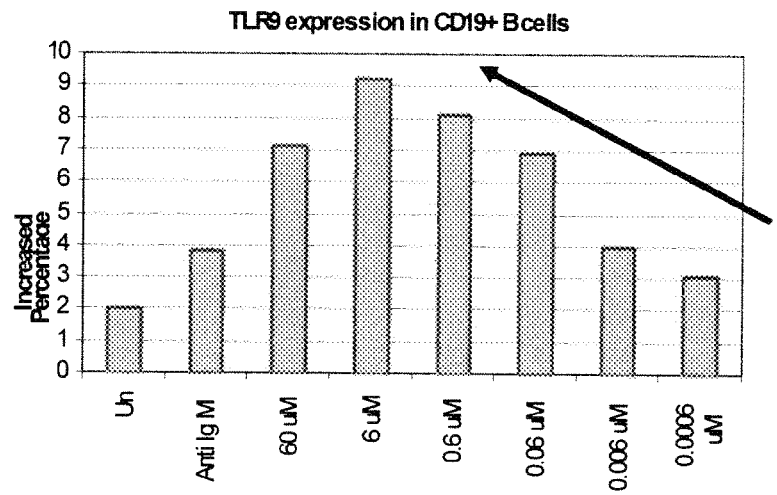

FIG. 8D.

1,3-dioxo-(2,6-dioxopiperidin-3-yl)-4-aminoisoindoline enhances TLR9 expression with anti-BCR

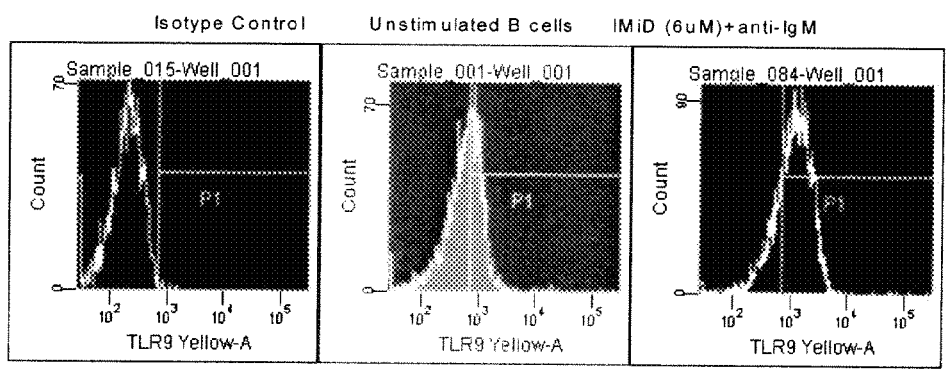

FIG. 8. TLR9 expression levels in 1,3-dioxo-(2,6-dioxopiperidin-3-yl)-4-aminoisoindoline treated normal B cells in the presence of anti IgM, IL-4 and anti CD40 for 3 days. (A) 1,3-dioxo-(2,6-dioxopiperidin-3-yl)-4-aminoisoindoline increases TLR9 expression in presence of stimuli. (B) 1,3-dioxo-(2,6-dioxopiperidin-3-yl)-4-aminoisoindoline dose dependently increases TLR9 expression with anti CD40 and IL-4. (C) 1,3-dioxo-(2,6-dioxopiperidin-3-yl)-4-aminoisoindoline dose dependently increases TLR9 expression with anti IgM. (D) Enhancement of TLR9 expression by 1,3-dioxo-(2,6-dioxopiperidin-3-yl)-4-aminoisoindoline with anti IgM.

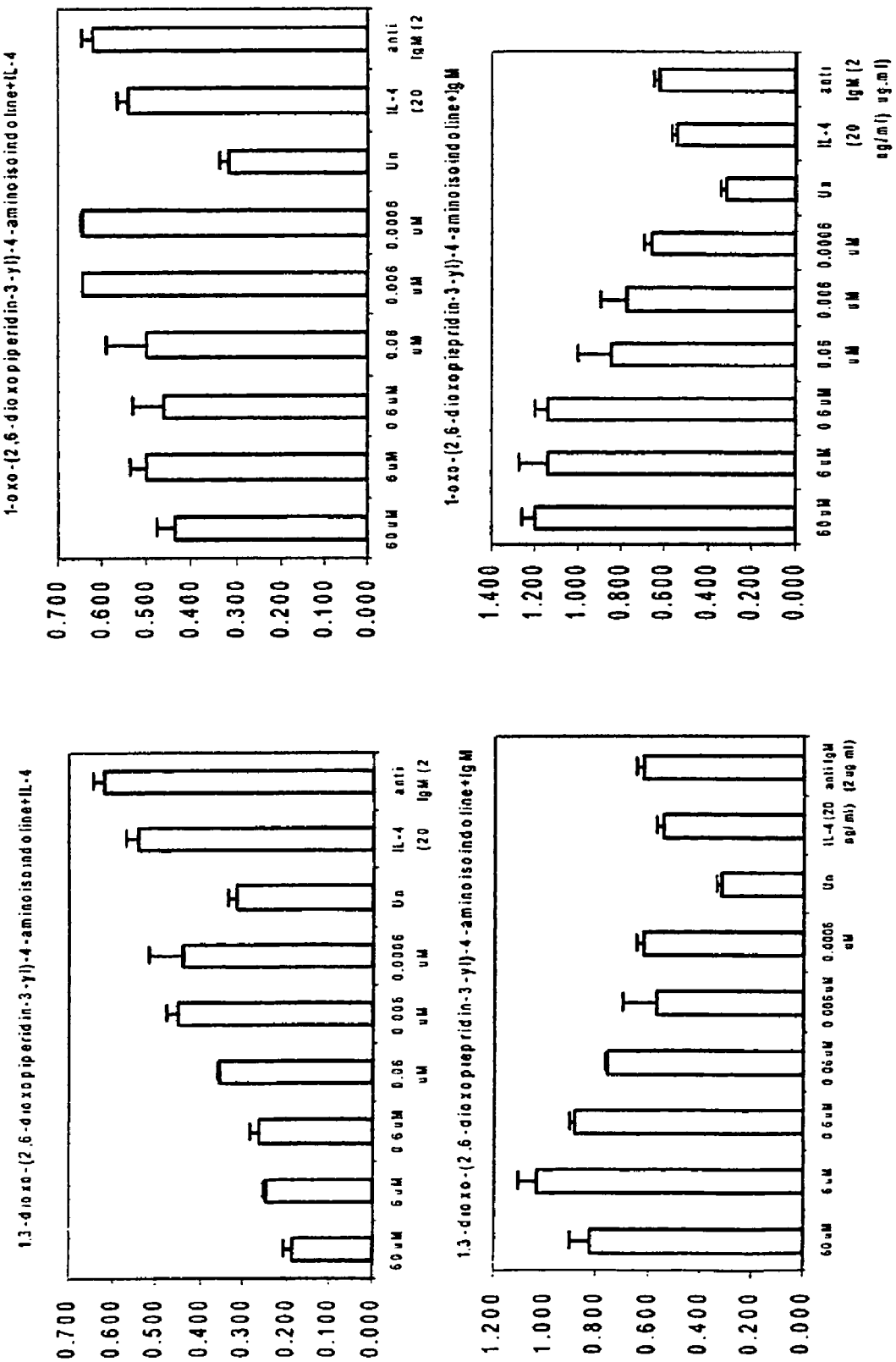

1,3-dioxo-(2,6-dioxopiperidin-3-yl)-4-aminoisoindoline with cytokines enhance B cell proliferation 1,3-dioxo-(2,6-dioxopiperidin-3-yl)-4-aminoisoindoline (IMiD 1) and 1-oxo-(2,6-dioxopiperidin-3-yl)-4-aminoisoindoline (IMiD 2) do not inhibit CD69 expression in IL-4 stimulated CD19+ B cells (n=3)

IMIDS do not inhibit CD69 expression in IL-4 stimulated CD19+ B cells (n=3)

IgE synthesis mediated by anti CD40+IL-4 in PBMC (21 days)
(IMiD 1: 1,3,-dioxo-(2,6-dioxopiperidin-3-yl)-4-aminoisoindoline;
IMiD 2: 1-oxo-(2,6-dioxopiperidin-3-yl)-4-aminoisoindoline)

IMIDS inhibit CD40+IL-4 mediated CSR to IgE in PBMCs $IC_{50}$ = 0.1 µM (1,3-dioxo-(2,6-dioxopiperidin-3-yl)-4-aminoisoindoline)
$IC_{50}$ = 0.3 µM (1-oxo-(2,6-dioxopiperidin-3-yl)-4-aminoisoindoline)

IMID inhibits IgG$_1$ subclass synthesis

1,3-dioxo-(2,6-dioxopiperidin-3-yl)-4-aminoisoindoline inhibits phospho-STAT6 in IL-4 stimulated CD19$^+$ B cells

No effect of 1,3-dioxo-(2,6-dioxopiperidin-3-yl)-4-aminoisoindoline on CD40 +IL-4 mediated HLA-DR expression

1,3-dioxo-(2,6-dioxo-piperidin-3-yl)-4-aminoisoindloine enhances BAFF mediated HLA-DR expression

METHODS AND COMPOSITIONS USING IMMUNOMODULATORY COMPOUNDS FOR THE TREATMENT OF IMMUNODEFICIENCY DISORDERS

This application claims the benefit of U.S. Provisional Application No. 60/631,870, filed Dec. 1, 2004, the entirety of which is incorporated herein by reference.

1. FIELD OF THE INVENTION

This invention relates to methods of treating, preventing and/or managing immunodeficiency disorders by the administration of one or more immunomodulatory compounds alone or in combination with other therapeutics. In particular, the invention encompasses the use of specific combinations, or "cocktails," of drugs and other conventional therapies. The invention also relates to pharmaceutical compositions and dosing regimens.

2. BACKGROUND OF THE INVENTION

2.1 Immunodeficiency Diseases

Immunodeficiency diseases are generally classified into one of two categories; primary and secondary. Secondary immunodeficiency diseases occur as a result of an underlying disease. Typically, once the underlying disease is treated, the immunodeficiency is reversed. Primary immunodeficiency diseases occur in the absence of, or independently from, underlying diseases. Immunoglobulin deficiency syndromes, which occur due to defective B-cells or antibodies, account for about 50% of all primary immunodeficiencies.

X-linked agammaglobulinemia is an inherited disease. The defect is more frequently observed in males than in females. Mature B-cells are capable of making antibodies and developing "memory," a feature in which the B-cell will rapidly recognize and respond to an infectious agent the next time it is encountered. All classes of antibodies are known to be decreased in agammaglobulinemia.

IgA deficiency is a disorder of the immune system characterized by increased susceptibility to infection. Patients with the disease fail to produce normal amounts of IgA. IgA provides the first line of defense for the inner surfaces of the body against infections of the lung, the intestine, the mouth, the urogenital tract and other areas lined by mucosal membranes. It is believed that IgA deficiency may result from the failure of B lymphocyte to mature into plasma cells that produce IgA antibodies. IgA deficiency is the most common disorder of the antibody system. Symptomatic patients suffer from recurrent and serious infections, including infections of the gastrointestinal tract, lungs, and sinuses, as well as allergic disorders, epilepsy, and cancer. There are currently no known therapies that address the underlying cause of IgA deficiency.

Transient hypo-gammaglobulinemia of infancy is a temporary disease of unknown cause. It is believed to be due to a defect in the development of T-helper cells, which recognize foreign antigens and activate T- and B-cells in an immune response. As the patient ages, the number and condition of T-helper cells may improve. Hypo-gammaglobulinemia is characterized by low levels of antibodies in the blood. During the disease period, patients have decreased levels of IgG and IgA antibodies that do not react well with infectious agents.

Common variable immunodeficiency (CVID) is a group of immunodeficiency syndromes in which B cell immunity is abnormal. Most patients have normal or near-normal numbers of circulating B cells, but the cells fail to differentiate into effective plasma B cells. As a result, patients have low or undetectable amounts of serum antibodies. The condition may result from insufficient stimulation of B cells rather than from a failure intrinsic to B cells. There are several thousand CVID patients in the U.S. and Europe, and CVID occurs equally in both genders. Most patients experience acute, recurring bacterial infections including pneumonia, bronchitis, and sinusitis. Current treatment involves regular administration of intravenous antibodies, which are prepared from pooled blood samples from thousands of individual donors.

Ig heavy chain deletions is a genetic disease in which part of the antibody molecule is not produced. It results in the loss of several antibody classes and subclasses, including most IgG antibodies and all IgA and IgE antibodies. It is believed that the disease occurs because part of the gene for the heavy chain has been lost.

Selective IgG subclass deficiencies are a group of genetic diseases in which some of the subclasses of IgG are not made. There are four subclasses in the IgG class of antibodies. As the B-cell matures, it can switch from one subclass to another. In these diseases, there is a defect in the maturation of the B-cells that results in a lack of switching.

IgG deficiency with hyper-IgM is a disease that results when the B-cell fails to switch from making IgM to IgG. This produces an increase in the amount of IgM antibodies present and a decrease in the amount of IgG antibodies. This disease is the result of a generic mutation.

Although various conventional therapies are currently being contemplated for immunodeficiency diseases, an ongoing need still exists for safe, effective and convenient therapies of these diseases.

2.2 IMiDS™

A number of studies have been conducted with the aim of providing compounds that can safely and effectively be used to treat diseases associated with abnormal production of TNF-α. See, e.g., Marriott, J. B., et al., *Expert Opin. Biol. Ther.* 1(4):1-8 (2001); G. W. Muller, et al., *Journal of Medicinal Chemistry,* 39(17): 3238-3240 (1996); and G. W. Muller, et al., *Bioorganic & Medicinal Chemistry Letters,* 8: 2669-2674 (1998). Some studies have focused on a group of compounds selected for their capacity to potently inhibit TNF-α production by LPS stimulated PBMC. L. G. Corral, et al., Ann. Rheum. Dis. 58:(Suppl 1) 1107-1113 (1999). These compounds, which are referred to as IMiDS™ (Celgene Corporation) or Immunomodulatory Drugs, show not only potent inhibition of TNF-α but also marked inhibition of LPS induced monocyte IL 13 and IL 12 production. LPS induced IL6 is also inhibited by immunomodulatory compounds, albeit partially. These compounds are potent stimulators of LPS induced IL10. Id. Particular examples of IMiD™s include, but are not limited to, the substituted 2-(2,6-dioxopiperidin-3-yl) phthalimides and substituted 2-(2,6-dioxopiperidin-3-yl)-1-oxoisoindoles described in U.S. Pat. Nos. 6,281,230 and 6,316,471, both to G. W. Muller, et al.

3. SUMMARY OF THE INVENTION

This invention encompasses methods of treating, preventing and/or managing immunodeficiency diseases or disorders. The methods comprise administering to a patient in need of such treatment, prevention, or management a therapeutically or prophylactically effective amount of an immunomodulatory compound, or a pharmaceutically acceptable salt, solvate (e.g., hydrate), stereoisomer, or prodrug thereof.

In some embodiments, an immunomodulatory compound is administered in combination with a therapy conventionally used to treat, prevent or manage immunodeficiency diseases or disorders.

This invention also encompasses methods of boosting humoral immunity in a patient in need of such boost (e.g., persons who may be exposed to pathogens). It is believed that an enhanced immune response to an immunogen can be obtained by administering to a patient a prophylactically effective amount of an immunomodulatory compound, or a pharmaceutically acceptable salt, solvate, stereoisomer, or prodrug thereof, prior to the patient's exposure to the immunogen.

In other methods of the invention, an immunomodulatory compound is administered in combination with a therapy conventionally used to treat, prevent or manage immunodeficiency diseases or disorders.

4. BRIEF DESCRIPTION OF THE FIGURES

FIG. 2A illustrates the up-regulation of CD40 by an immunomodulatory compound on normal B cells treated with BAFF (also known as TALL-1, zTNF4, THANK, BlyS, or TNFSF-20) or LPS (lipopolysaccharide).

FIG. 2B illustrates the up-regulation of HLA-DR by an immunomodulatory compound on normal B cells treated with BAFF or LPS.

FIG. 3A illustrates the FACS analysis, showing an increased CD69 expression in $CD19^+$ B cells treated with an immunomodulatory compound.

FIG. 3B also illustrates the FACS analysis, showing an increased CD69 expression in $CD19^+$ B cells treated with another immunomodulatory compound.

FIG. 4 illustrates an enhanced TNFα production in activated CD 19+ cells treated with different immunomodulatory compounds.

FIG. 5 illustrates a dose-dependent increase in IL-6 expression by an immunomodulatory compound.

FIG. 6 illustrates morphological changes in B-lymphocytes co-activated with an immunomodulatory compound.

Figure 7A:
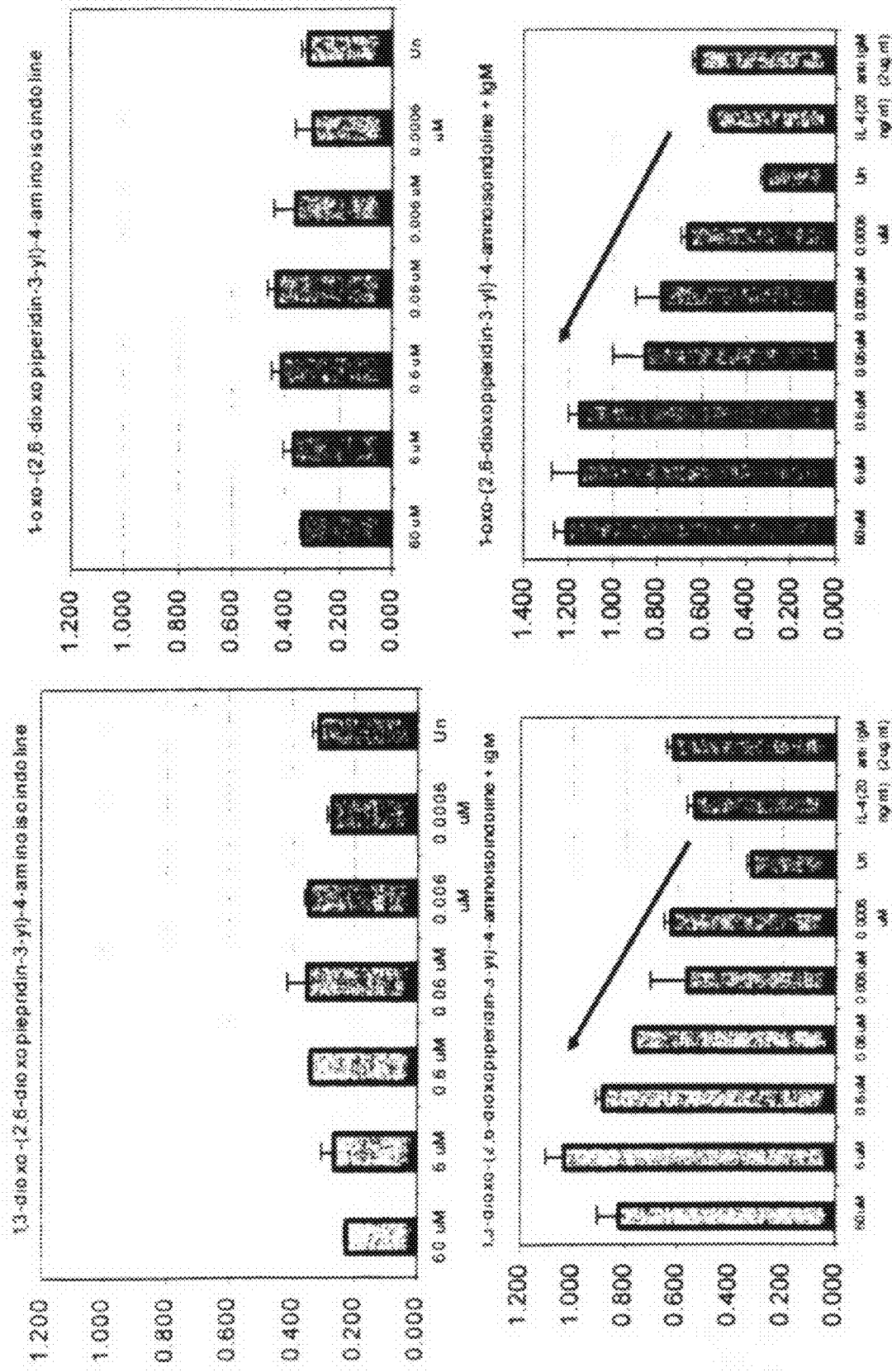

FIG. 7A illustrates co-stimulation of B cell proliferation by immunomodulatory compounds.

FIG. 7B illustrates comparison of morphological changes in stimulated B cells.

FIG. 7C illustrates promotion of LPS and BAFF stimulated cell proliferation by an immunomodulatory compound.

Figure 8A:
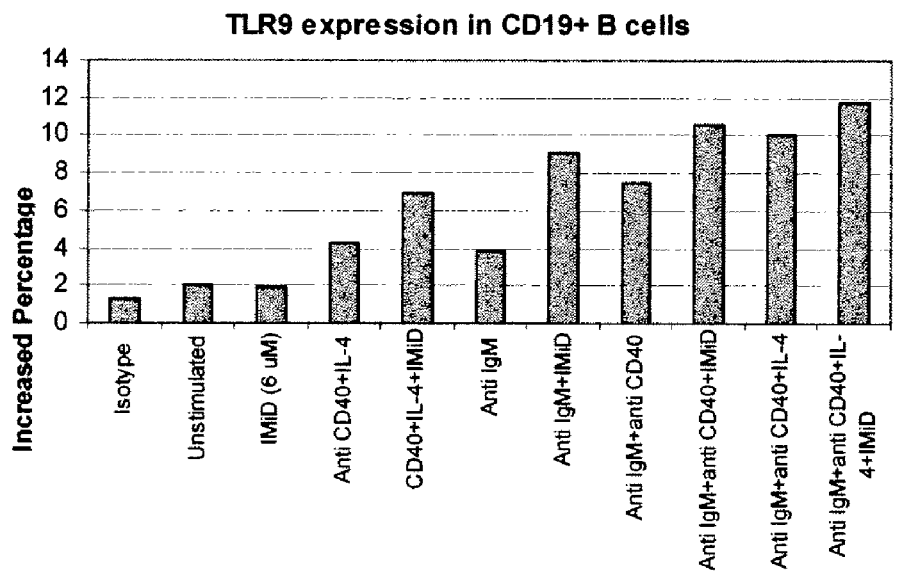

FIG. 8A illustrates increased TLR 9 (Toll-Like Receptor 9) expression in B cells co-stimulated with an immunomodulatory compound.

Figure 8B:
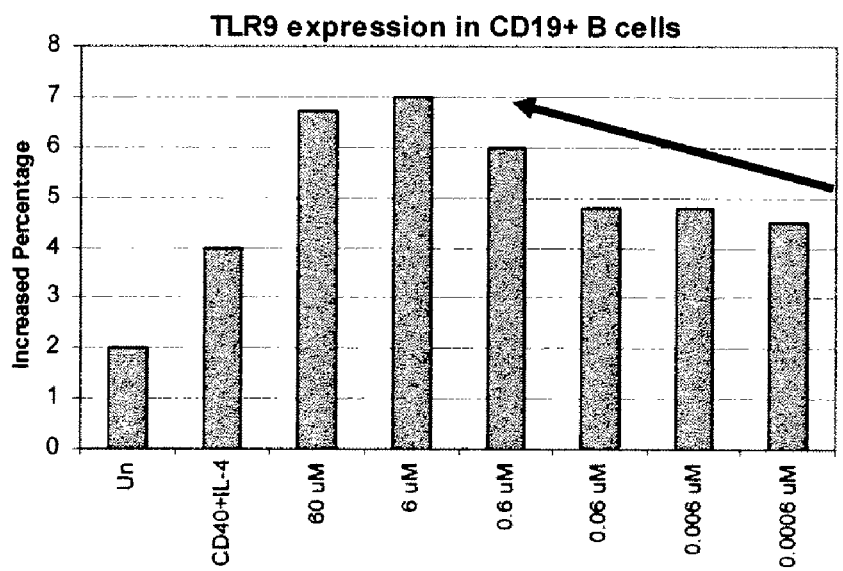

FIG. 8B illustrates increased TLR 9 expression in B cells stimulated with an immunomodulatory compound, anti CD40, and IL-4.

FIGS. 8C and D illustrate increased TLR 9 expression in B cells stimulated with an immunomodulatory compound and anti IgM.

FIG. 9A illustrates inhibition of IL-4 signaling by immunomodulatory compounds.

Figure 9B:
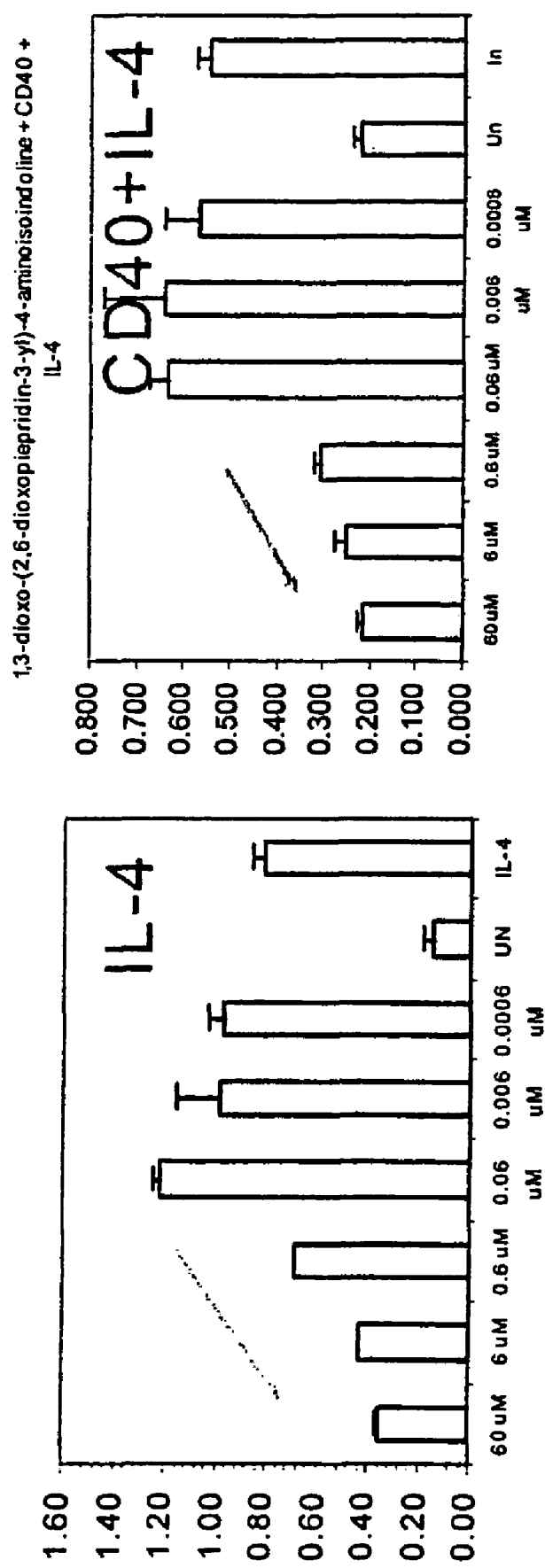

FIG. 9B illustrates inhibition of IL-4 or (anti CD40+IL-4) mediated B cell proliferation by an immunomodulatory compound.

Figure 9C:
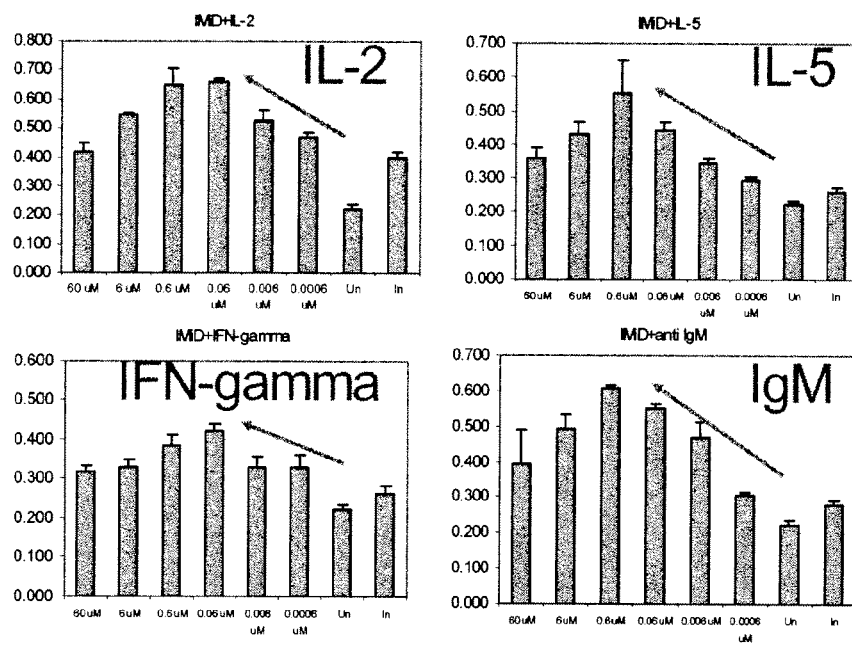

FIG. 9C illustrates promotional effects of an immunomodulatory compound on various cytokines mediated B cell proliferation.

Figure 9D:
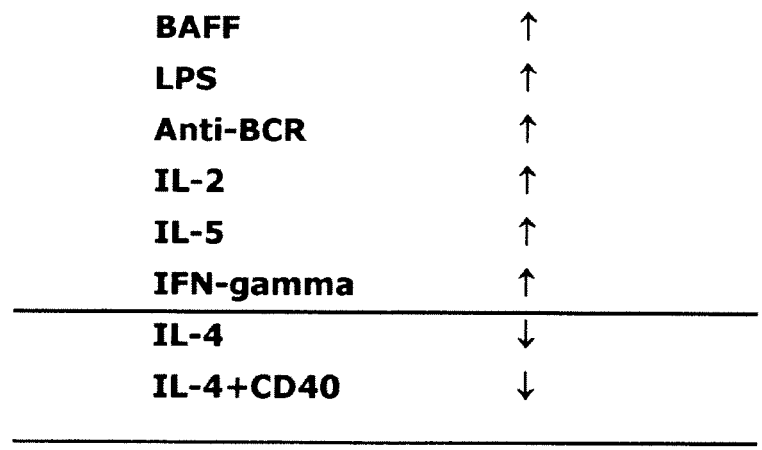

FIG. 9D illustrates a summary of immunomodulatory compounds' effect on cytokine mediated B cell proliferation.

Figure 10A:
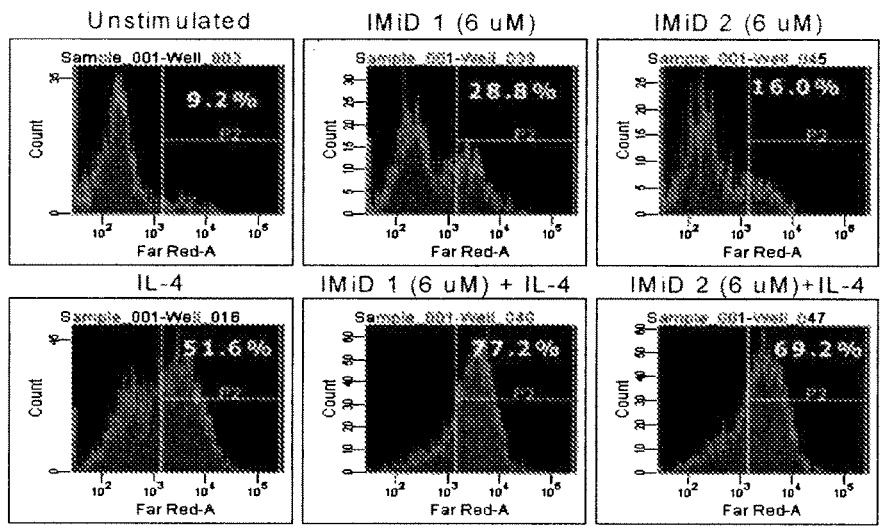
Figure 10B:
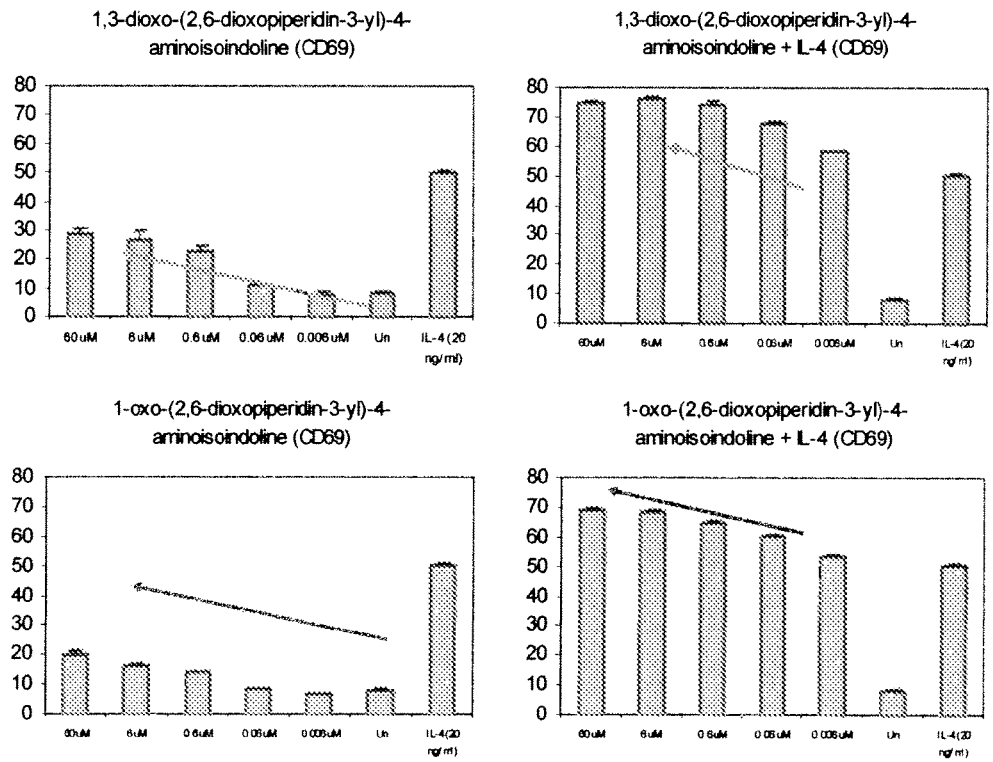

FIGS. 10A and B illustrate no inhibitory effect of immunomodulatory compounds on CD69 expression in IL-4 stimulated B cells.

Figure 11A:
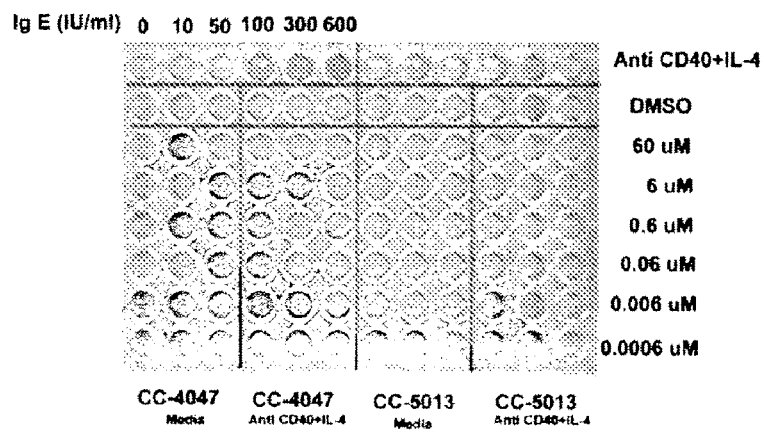
Figure 11B:
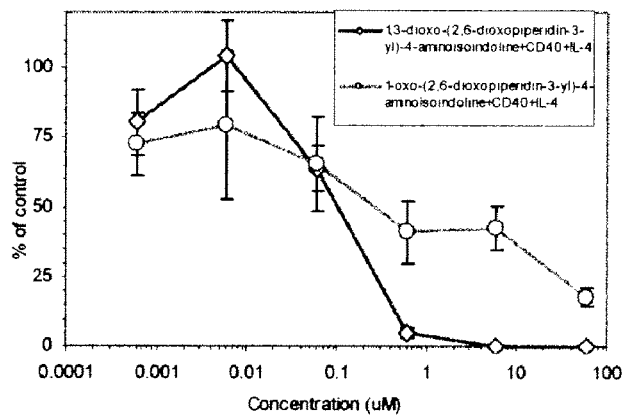

FIGS. 11A and B illustrate inhibition of IgE synthesis by immunomodulatory compounds.

Figure 11C:
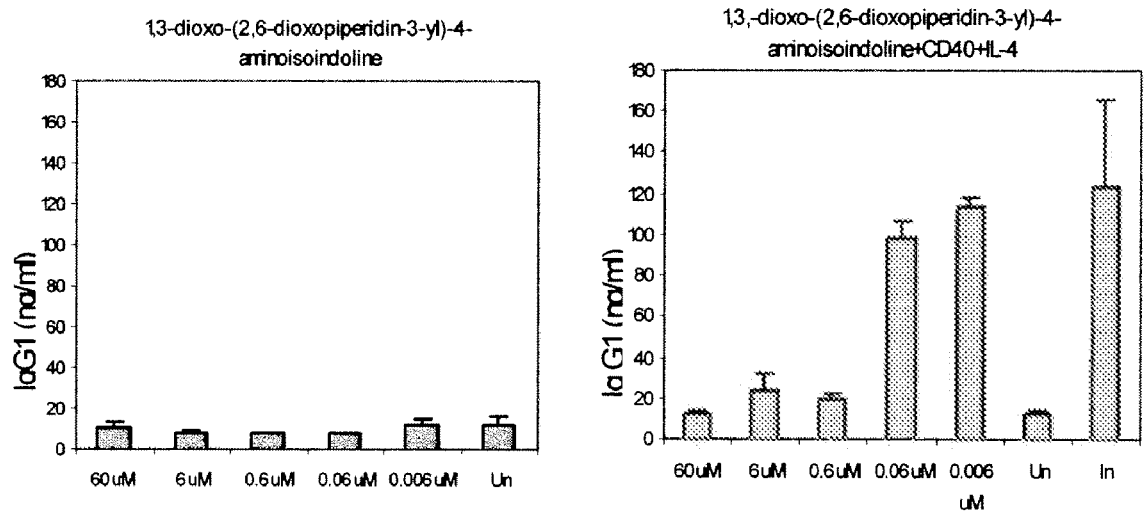

FIG. 11C illustrates inhibition of $IgG_1$ synthesis by an immunomodulatory compound.

Figure 11D:
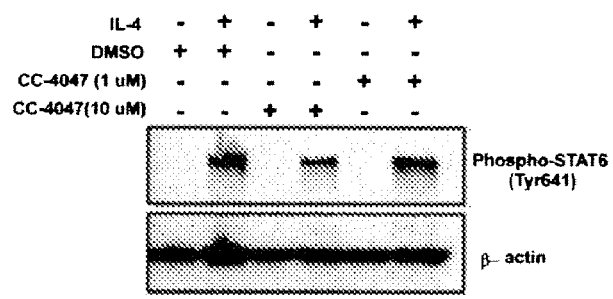

FIG. 11D illustrates inhibition of phospho-STAT6 by an immunomodulatory compound in IL-4 stimulated B cells.

Figure 11E:
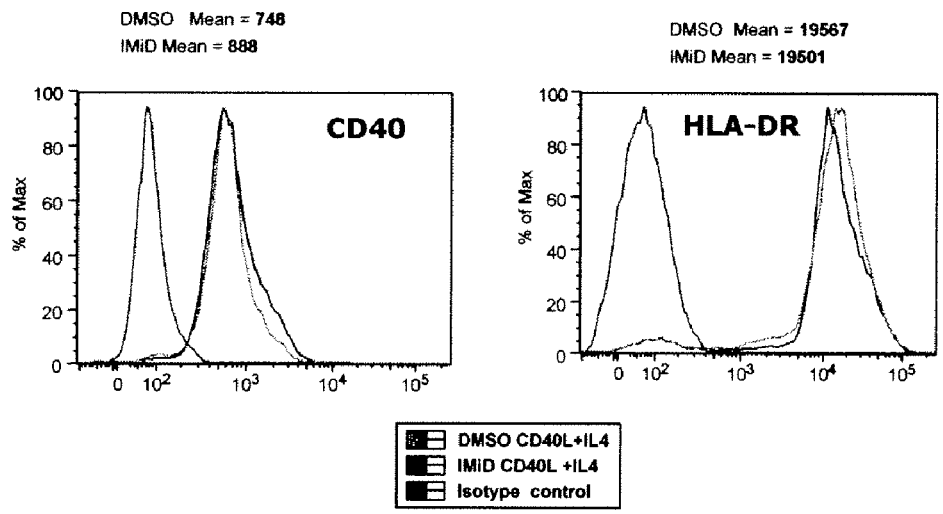

FIG. 11E illustrates no effect by an immunomodulatory compound on CD40+IL-4 mediated HLA-DR expression.

Figure 11F:
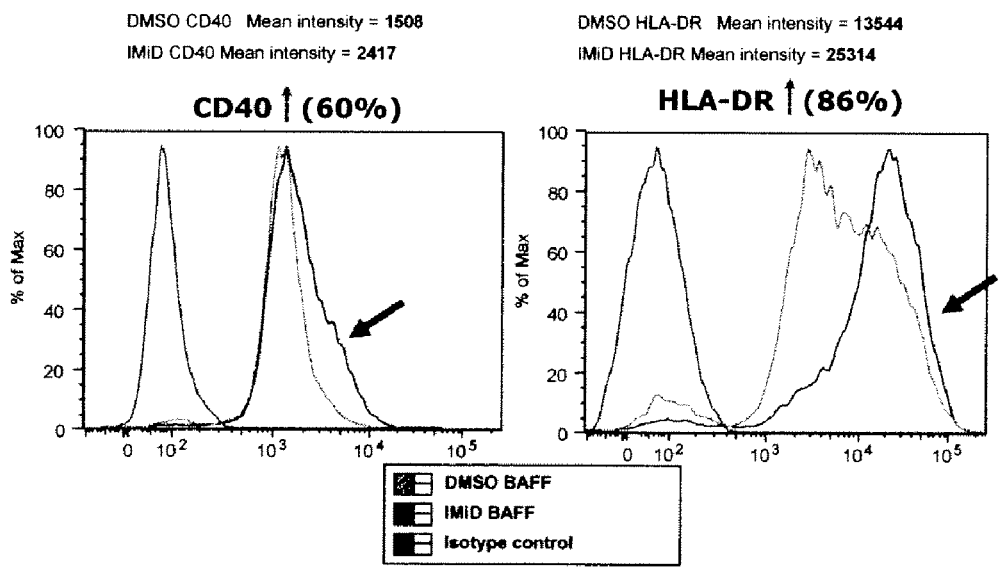

FIG. 11F illustrates promotional effects of an immunomodulatory compound on CD40 and HLA-DR expressions in BAFF treated B cells.

5. DETAILED DESCRIPTION OF THE INVENTION

A first embodiment of the invention encompasses methods of treating, managing, and/or preventing an immunodeficiency disease or disorder which comprises administering to a patient in need of such treatment or prevention a therapeutically or prophylactically effective amount of an immunomodulatory compound of the invention, or a pharmaceutically acceptable salt, solvate, stereoisomer, or prodrug thereof.

In particular methods encompassed by this embodiment, the immunomodulatory compound is administered in combination with another drug ("second active agent") or method of treating, managing, and/or preventing an immunodeficiency disease or disorder. Second active agents include small molecules and large molecules (e.g., proteins and antibodies), examples of which are provided herein, as well as stem cells. Methods, or therapies, that can be used in combination with the administration of the immunomodulatory compound include, but are not limited to, antibody injections or infusions, and stem cell transplantation.

Examples of immunodeficiency diseases or disorders include, but not limited to, adenosine deaminase deficiency, antibody deficiency with normal or elevated Igs, ataxia-tenlangiectasia, bare lymphocyte syndrome, common variable immunodeficiency, Ig deficiency with hyper-IgM, Ig heavy chain deletions, IgA deficiency, immunodeficiency with thymoma, reticular dysgenesis, Nezelof syndrome, selective IgG subclass deficiency, transient hypogammaglobulinemia of infancy, Wistcott-Aldrich syndrome, X-linked agammaglobulinemia, X-linked severe combined immunodeficiency.

5.1 Definitions

As used herein, and unless otherwise specified, the term "pharmaceutically acceptable salt" refers to salts prepared from pharmaceutically acceptable non-toxic acids, including inorganic acids and organic acids. Suitable non-toxic acids include inorganic and organic acids such as, but not limited to, acetic, alginic, anthranilic, benzenesulfonic, benzoic, camphorsulfonic, citric, ethenesulfonic, formic, fumaric, furoic, gluconic, glutamic, glucorenic, galacturonic, glycidic, hydrobromic, hydrochloric, isethionic, lactic, maleic, malic, mandelic, methanesulfonic, mucic, nitric, pamoic, pantothenic, phenylacetic, propionic, phosphoric, salicylic, stearic, succinic, sulfanilic, sulfuric, tartaric acid, p-toluenesulfonic and the like. Suitable are hydrochloric, hydrobromic, phosphoric, and sulfuric acids.

As used herein, and unless otherwise specified, the term "solvate" means a compound of the present invention or a salt thereof, that further includes a stoichiometric or non-stoichiometric amount of solvent bound by non-covalent intermolecular forces. Where the solvent is water, the solvate is a hydrate.

As used herein, and unless otherwise specified, the term "prodrug" means a derivative of a compound that can hydrolyze, oxidize, or otherwise react under biological conditions (in vitro or in vivo) to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include compounds that comprise —NO, —NO$_2$, —ONO, or —ONO$_2$ moieties. Prodrugs can typically be prepared using well-known methods, such as those described in *Burger's Medicinal Chemistry and Drug Discovery,* 172-178, 949-982 (Manfred E. Wolff ed., 5th ed. 1995), and *Design of Prodrugs* (H. Bundgaard ed., Elselvier, N.Y. 1985).

As used herein, and unless otherwise specified, the terms "biohydrolyzable carbamate," "biohydrolyzable carbonate," "biohydrolyzable ureide" and "biohydrolyzable phosphate" mean a carbamate, carbonate, ureide and phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, and unless otherwise specified, the term "stereoisomer" encompasses all enantiomerically/stereomerically pure and enantiomerically/stereomerically enriched compounds of this invention.

As used herein, and unless otherwise indicated, the term "stereomerically pure" or "enantiomerically pure" means that a compound comprises one stereoisomer and is substantially free of its counter stereoisomer or enantiomer. For example, a compound is stereomerically or enantiomerically pure when the compound contains 80%, 90%, or 95% or more of one stereoisomer and 20%, 10%, or 5% or less of the counter stereoisomer. In certain cases, a compound of the invention is considered optically active or stereomerically/enantiomerically pure (i.e., substantially the R-form or substantially the S-form) with respect to a chiral center when the compound is about 80% ee (enantiomeric excess) or greater, preferably, equal to or greater than 90% ee with respect to a particular chiral center, and more preferably 95% ee with respect to a particular chiral center.

As used herein, and unless otherwise indicated, the term "stereomerically enriched" or "enantiomerically enriched" encompasses racemic mixtures as well as other mixtures of stereoisomers of compounds of this invention (e.g., R/S=30/70, 35/65, 40/60, 45/55, 55/45, 60/40, 65/35 and 70/30).

As used herein, and unless otherwise specified, the terms "treat," "treating" and "treatment" contemplate an action that occurs while a patient is suffering from the specified disease or disorder, which reduces the severity of the disease or disorder, or retards or slows the progression of the disease or disorder.

As used herein, unless otherwise specified, the terms "prevent," "preventing" and "prevention" contemplate an action that occurs before a patient begins to suffer from the specified disease or disorder, which inhibits or reduces the severity of the disease or disorder.

As used herein, and unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

As used herein, and unless otherwise specified, the term "therapeutically effective amount" of a compound is an amount sufficient to provide a therapeutic benefit in the treatment or management of a disease or condition, or to delay or minimize one or more symptoms associated with the disease or condition. A therapeutically effective amount of a compound means an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, the term "prophylactically effective amount" of a compound is an amount sufficient to prevent a disease or condition, or one or more symptoms associated with the disease or condition, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

5.2 Immunomodulatory Compounds

Compounds of the invention can either be commercially purchased or prepared according to the methods described in the patents or patent publications disclosed herein. Further, optically pure compositions can be asymmetrically synthesized or resolved using known resolving agents or chiral columns as well as other standard synthetic organic chemistry techniques. Compounds used in the invention may include immunomodulatory compounds that are racemic, stereomerically enriched or stereomerically pure, and pharmaceutically acceptable salts, solvates, stereoisomers, and prodrugs thereof.

Compounds used in the invention may be small organic molecules having a molecular weight less than about 1,000 g/mol, and are not proteins, peptides, oligonucleotides, oligosaccharides or other macromolecules.

As used herein and unless otherwise indicated, the terms "immunomodulatory compounds" and "IMiDs™" (Celgene Corporation) encompasses small organic molecules that markedly inhibit TNF-α, LPS induced monocyte IL1β and IL12, and partially inhibit IL6 production. Specific immunomodulatory compounds are discussed below.

TNF-α is an inflammatory cytokine produced by macrophages and monocytes during acute inflammation. TNF-α is responsible for a diverse range of signaling events within cells. Without being limited by theory, one of the biological effects exerted by the immunomodulatory compounds of the invention is the reduction of synthesis of TNF-α. Immunomodulatory compounds of the invention enhance the degradation of TNF-α mRNA.

Further, without being limited by theory, immunomodulatory compounds used in the invention may also be potent co-stimulators of T cells and increase cell proliferation dramatically in a dose dependent manner. Immunomodulatory compounds of the invention may also have a greater co-stimulatory effect on the CD8+ T cell subset than on the CD4+ T cell subset. In addition, the compounds preferably have anti-inflammatory properties, and efficiently co-stimulate T cells. Further, without being limited by a particular theory, immunomodulatory compounds used in the invention may be capable of acting both indirectly through cytokine activation and directly on Natural Killer ("NK") cells, and increase the NK cells' ability to produce beneficial cytokines such as, but not limited to, IFN-γ.

Specific examples of immunomodulatory compounds, include, but are not limited to, cyano and carboxy derivatives of substituted styrenes such as those disclosed in U.S. Pat. No. 5,929,117; 1-oxo-2-(2,6-dioxo-3-fluoropiperidin-3-yl) isoindolines and 1,3-dioxo-2-(2,6-dioxo-3-fluoropiperidine-3-yl) isoindolines such as those described in U.S. Pat. Nos. 5,874,448 and 5,955,476; the tetra substituted 2-(2,6-dioxopiperdin-3-yl)-1-oxoisoindolines described in U.S. Pat. No. 5,798,368; 1-oxo and 1,3-dioxo-2-(2,6-dioxopiperidin-3-yl) isoindolines (e.g., 4-methyl derivatives of thalidomide), including, but not limited to, those disclosed in U.S. Pat. Nos. 5,635,517, 6,476,052, 6,555,554, and 6,403,613; 1-oxo and 1,3-dioxoisoindolines substituted in the 4- or 5-position of the indoline ring (e.g., 4-(4-amino-1,3-dioxoisoindoline-2-yl)-4-carbamoylbutanoic acid) described in U.S. Pat. No. 6,380,239; isoindoline-1-one and isoindoline-1,3-dione substituted in the 2-position with 2,6-dioxo-3-hydroxypiperidin-5-yl (e.g., 2-(2,6-dioxo-3-hydroxy-5-fluoropiperidin-5-yl)-4-aminoisoindolin-1-one) described in U.S. Pat. No. 6,458,810; a class of non-polypeptide cyclic amides disclosed in U.S. Pat. Nos. 5,698,579 and 5,877,200; aminothalidomide, as well as analogs, hydrolysis products, metabolites, derivatives and precursors of aminothalidomide, and substituted 2-(2,6-dioxopiperidin-3-yl) phthalimides and substituted 2-(2,6-dioxopiperidin-3-yl)-1-oxoisoindoles such as those described in U.S. Pat. Nos. 6,281,230 and 6,316,471; and isoindole-imide compounds such as those described in U.S. patent application Ser. No. 09/972,487 filed on Oct. 5, 2001, U.S. patent application Ser. No. 10/032,286 filed on Dec. 21, 2001, and International Application No. PCT/US01/50401 (International Publication No. WO 02/059106). The entireties of each of the patents and patent applications identified herein are incorporated herein by reference. Immunomodulatory compounds do not include thalidomide.

Other specific immunomodulatory compounds of the invention include, but are not limited to, 1-oxo-and 1,3 dioxo-2-(2,6-dioxopiperidin-3-yl) isoindolines substituted with amino in the benzo ring as described in U.S. Pat. No. 5,635,517 which is incorporated herein by reference. These compounds have the structure I:

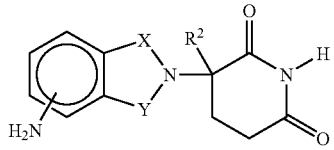

I in which one of X and Y is C=O, the other of X and Y is C=O or CH₂, and R² is hydrogen or lower alkyl, in particular methyl. Specific immunomodulatory compounds include, but are not limited to:
1-oxo-2-(2,6-dioxopiperidin-3-yl)-4-aminoisoindoline;
1-oxo-2-(2,6-dioxopiperidin-3-yl)-5-aminoisoindoline;
1-oxo-2-(2,6-dioxopiperidin-3-yl)-6-aminoisoindoline;
1-oxo-2-(2,6-dioxopiperidin-3-yl)-7-aminoisoindoline;
1,3-dioxo-2-(2,6-dioxopiperidin-3-yl)-4-aminoisoindoline; and
1,3-dioxo-2-(2,6-dioxopiperidin-3-yl)-5-aminoisoindoline.

Other specific immunomodulatory compounds of the invention belong to a class of substituted 2-(2,6-dioxopiperidin-3-yl) phthalimides and substituted 2-(2,6-dioxopiperidin-3-yl)-1-oxoisoindoles, such as those described in U.S. Pat. Nos. 6,281,230; 6,316,471; 6,335,349; and 6,476,052, and International Patent Application No. PCT/US97/13375 (International Publication No. WO 98/03502), each of which is incorporated herein by reference. Representative compounds are of formula:

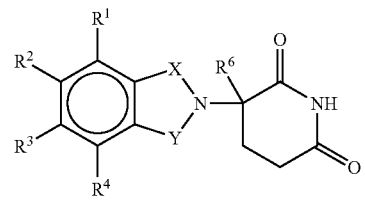

in which:
one of X and Y is C=O and the other of X and Y is C=O or CH₂;

(i) each of $R^1$, $R^2$, $R^3$, and $R^4$, independently of the others, is halo, alkyl of 1 to 4 carbon atoms, or alkoxy of 1 to 4 carbon atoms or (ii) one of $R^1$, $R^2$, $R^3$, and $R^4$ is —NHR$^5$ and the remaining of $R^1$, $R^2$, $R^3$, and $R^4$ are hydrogen;

$R^5$ is hydrogen or alkyl of 1 to 8 carbon atoms;

$R^6$ is hydrogen, alkyl of 1 to 8 carbon atoms, benzyl, or halo;

provided that $R^6$ is other than hydrogen if X and Y are C=O and (i) each of $R^1$, $R^2$, $R^3$, and $R^4$ is fluoro or (ii) one of $R^1$, $R^2$, $R^3$, or $R^4$ is amino.

Compounds representative of this class are of the formulas:

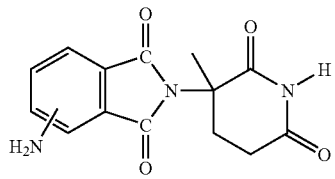

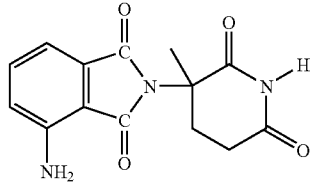

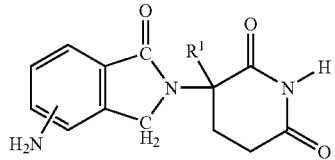

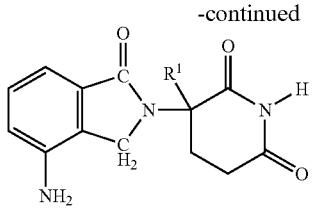

wherein $R^1$ is hydrogen or methyl. In a separate embodiment, the invention encompasses the use of enantiomerically pure forms (e.g. optically pure (R) or (S) enantiomers) of these compounds.

Still other specific immunomodulatory compounds of the invention belong to a class of isoindole-imides disclosed in U.S. Patent Application Publication Nos. US 2003/0096841 and US 2003/0045552, and International Application No. PCT/US01/50401 (International Publication No. WO 02/059106), each of which are incorporated herein by reference. Representative compounds are of formula II:

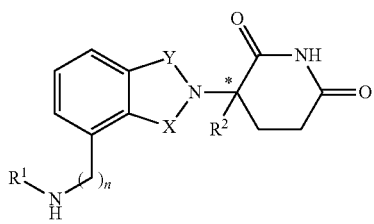

and pharmaceutically acceptable salts, hydrates, solvates, clathrates, enantiomers, diastereomers, racemates, and mixtures of stereoisomers thereof, wherein:

one of X and Y is C=O and the other is $CH_2$ or C=O;

$R^1$ is H, $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$C_1-C_6$)heterocycloalkyl, $(C_0-C_4)$alkyl-$(C_2-C_5)$heteroaryl, $C(O)R^3$, $C(S)R^3$, $C(O)OR^4$, $(C_1-C_8)$alkyl-$N(R^6)_2$, $(C_1-C_8)$alkyl-$OR^5$, $(C_1-C_8)$alkyl-$C(O)OR^5$, $C(O)NHR^3$, $C(S)NHR^3$, $C(O)NR^3R^{3'}$, $C(S)NR^3R^{3'}$ or $(C_1-C_8)$alkyl-$O(CO)R^5$;

$R^2$ is H, F, benzyl, $(C_1-C_8)$alkyl, $(C_2-C_8)$alkenyl, or $(C_2-C_8)$alkynyl;

$R^3$ and $R^{3'}$ are independently $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$C_1-C_6$)heterocycloalkyl, $(C_0-C_4)$alkyl-$C_2-C_5$)heteroaryl, $(C_0-C_8)$alkyl-$N(R^6)_2$, $(C_1-C_8)$alkyl-$OR^5$, $(C_1-C_8)$alkyl-$C(O)OR^5$, $(C_1-C_8)$alkyl-$O(CO)R^5$, or $C(O)OR^5$;

$R^4$ is $(C_1-C_8)$alkyl, $(C_2-C_8)$alkenyl, $(C_2-C_8)$alkynyl, $(C_1-C_4)$alkyl-$OR^5$, benzyl, aryl, $(C_0-C_4)$alkyl-$C_1-C_6$)heterocycloalkyl, or $(C_0-C_4)$alkyl-$(C_2-C_5)$heteroaryl;

$R^5$ is $(C_1-C_8)$alkyl, $(C_2-C_8)$alkenyl, $(C_2-C_8)$alkynyl, benzyl, aryl, or $(C_2-C_5)$heteroaryl;

each occurrence of $R^6$ is independently H, $(C_1-C_8)$alkyl, $(C_2-C_8)$alkenyl, $(C_2-C_8)$alkynyl, benzyl, aryl, $(C_2-C_5)$heteroaryl, or $(C_0-C_8)$alkyl-$C(O)O$—$R^5$ or the $R^6$ groups can join to form a heterocycloalkyl group;

n is 0 or 1; and

* represents a chiral-carbon center.

In specific compounds of formula II, when n is 0 then $R^1$ is $(C_3-C_7)$cycloalkyl, $(C_2-C_8)$alkenyl, $(C_2-C_8)$alkynyl, benzyl, aryl, $(C_0-C_4)$alkyl-$C_1-C_6$)heterocycloalkyl, $(C_0-C_4)$alkyl-$(C_2-C_5)$heteroaryl, $C(O)R^3$, $C(O)OR^4$, $(C_1-C_8)$alkyl-$N(R^6)_2$, $(C_1-C_8)$alkyl-$OR^5$, $(C_1-C_8)$alkyl-$C(O)OR^5$, $C(S)NHR^3$, or $(C_1-C_8)$alkyl-$O(CO)R^5$;

$R^2$ is H or $(C_1-C_8)$alkyl; and $R^3$ is $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$C_1-C_6$)heterocycloalkyl, $(C_0-C_4)$alkyl-$C_2-C_5$)heteroaryl, $(C_5-C_8)$alkyl-$N(R^6)_2$; $(C_0-C_8)$alkyl-$NH$—$C(O)O$—$R^5$; $(C_1-C_8)$alkyl-$OR^5$, $(C_1-C_8)$alkyl-$C(O)OR^5$, $(C_1-C_8)$alkyl-$O(CO)R^5$, or $C(O)OR^5$; and the other variables have the same definitions.

In other specific compounds of formula II, $R^2$ is H or $(C_1-C_4)$alkyl.

In other specific compounds of formula II, $R^1$ is $(C_1-C_8)$alkyl or benzyl.

In other specific compounds of formula II, $R^1$ is H, $(C_1-C_8)$alkyl, benzyl, $CH_2OCH_3$, $CH_2CH_2OCH_3$, or

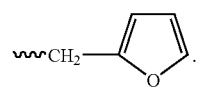

In another embodiment of the compounds of formula II, $R^1$ is

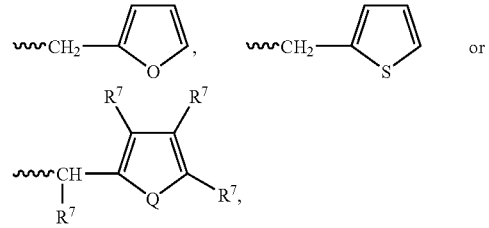

wherein Q is O or S, and each occurrence of $R^7$ is independently H, $(C_1-C_8)$alkyl, $(C_3-C_7)$cycloalkyl, $(C_2-C_8)$alkenyl, $(C_2-C_8)$alkynyl, benzyl, aryl, halogen, $(C_0-C_4)$alkyl-$C_1-C_6$)heterocycloalkyl, $(C_0-C_4)$alkyl-$(C_2-C_5)$heteroaryl, $(C_0-C_8)$alkyl-$N(R^6)_2$, $(C_1-C_8)$alkyl-$OR^5$, $(C_1-C_8)$alkyl-$C(O)OR^5$, $(C_1-C_8)$alkyl-$O(CO)R^5$, or $C(O)OR^5$, or adjacent occurrences of $R^7$ can be taken together to form a bicyclic alkyl or aryl ring.

In other specific compounds of formula II, $R^1$ is $C(O)R^3$.

In other specific compounds of formula $I^1$, $R^3$ is $(C_0-C_4)$alkyl-$(C_2-C_5)$heteroaryl, $(C_1-C_8)$alkyl, aryl, or $(C_0-C_4)$alkyl-$OR^5$.

In other specific compounds of formula II, heteroaryl is pyridyl, furyl, or thienyl.

In other specific compounds of formula II, $R^1$ is $C(O)OR^4$.

In other specific compounds of formula II, the H of C(O) NHC(O) can be replaced with $(C_1-C_4)$alkyl, aryl, or benzyl.

Further examples of the compounds in this class include, but are not limited to: [2-(2,6-dioxo-piperidin-3-yl)-1,3-dioxo-2,3-dihydro-1H-isoindol-4-ylmethyl]-amide; (2-(2,6-dioxo-piperidin-3-yl)-1,3-dioxo-2,3-dihydro-1H-isoindol-4-ylmethyl)-carbamic acid tert-butyl ester; 4-(aminomethyl)-2-(2,6-dioxo(3-piperidyl))-isoindoline-1,3-dione; N-(2-(2,6-dioxo-piperidin-3-yl)-1,3-dioxo-2,3-dihydro-1H-isoindol-4-ylmethyl)-acetamide; N-{(2-(2,6-dioxo(3-piperidyl)-1,3-dioxoisoindolin-4-yl)methyl}cyclopropyl-carboxamide; 2-chloro-N-{(2-(2,6-dioxo(3-piperidyl))-1,3-dioxoisoindolin-4-yl)methyl}acetamide; N-(2-(2,6-dioxo(3-piperidyl))-1,3-dioxoisoindolin-4-yl)-3-pyridylcarboxamide; 3-{1-oxo-4-(benzylamino)isoindolin-2-yl}piperidine-2,6-dione; 2-(2,6-dioxo(3-piperidyl))-4-(benzylamino)isoindoline-1,3-dione; N-{(2-(2,6-dioxo(3-piperidyl))-1,3-dioxoisoindolin-4-yl)methyl}propanamide; N-{(2-(2,6-dioxo(3-piperidyl))-1,3-dioxoisoindolin-4-yl)methyl}-3-pyridylcarboxamide; N-{(2-(2,6-dioxo(3-piperidyl))-1,3-dioxoisoindolin-4-yl)methyl}heptanamide; N-{(2-(2,6-dioxo(3-piperidyl))-1,3-dioxoisoindolin-4-yl)methyl}2-furylcarboxamide; {N-(2-(2, 6-dioxo(3-piperidyl))-1,3-dioxoisoindolin-4-yl) carbamoyl}methyl acetate; N-(2-(2,6-dioxo(3-piperidyl))-1,3-dioxoisoindolin-4-yl)pentanamide; N-(2-(2,6-dioxo(3-piperidyl))-1,3-dioxoisoindolin-4-yl)-2-thienylcarboxamide; N-{[2-(2,6-dioxo(3-piperidyl))-1,3-dioxoisoindolin-4-yl]methyl}(butylamino)carboxamide; N-{[2-(2,6-dioxo(3-piperidyl))-1,3-dioxoisoindolin-4-yl]methyl}(octylamino)carboxamide; and N-{[2-(2,6-dioxo(3-piperidyl))-1,3-dioxoisoindolin-4-yl]methyl}(benzylamino)carboxamide.

Still other specific immunomodulatory compounds of the invention belong to a class of isoindole-imides disclosed in U.S. Patent Application Publication Nos. US 2002/0045643, International Publication No. WO 98/54170, and U.S. Pat. No. 6,395,754, each of which is incorporated herein by reference. Representative compounds are of formula III:

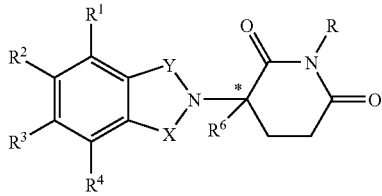

and pharmaceutically acceptable salts, hydrates, solvates, clathrates, enantiomers, diastereomers, racemates, and mixtures of stereoisomers thereof, wherein:
one of X and Y is C═O and the other is $CH_2$ or C═O;
R is H or $CH_2OCOR'$;
(i) each of $R^1$, $R^2$, $R^3$, or $R^4$, independently of the others, is halo, alkyl of 1 to 4 carbon atoms, or alkoxy of 1 to 4 carbon atoms or (ii) one of $R^1$, $R^2$, $R^3$, or $R^4$ is nitro or —$NHR^5$ and the remaining of $R^1$, $R^2$, $R^3$, or $R^4$ are hydrogen;
$R^5$ is hydrogen or alkyl of 1 to 8 carbons
$R^6$ hydrogen, alkyl of 1 to 8 carbon atoms, benzo, chloro, or fluoro;
R' is $R^7$—$CHR^{10}$—$N(R^8R^9)$;
$R^7$ is m-phenylene or p-phenylene or —$(C_nH_{2n})$— in which n has a value of 0 to 4;
each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2X_1CH_2CH_2$— in which $X_1$ is —O—, —S—, or —NH—;
$R^{10}$ is hydrogen, alkyl of to 8 carbon atoms, or phenyl; and
* represents a chiral-carbon center.
Other representative compounds are of formula:

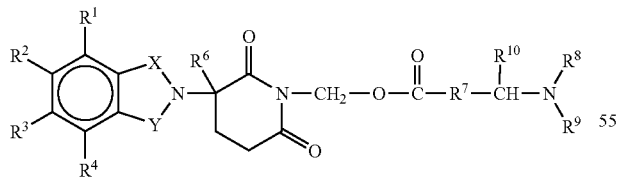

wherein:
one of X and Y is C═O and the other of X and Y is C═O or $CH_2$;
(i) each of $R^1$, $R^2$, $R^3$, or $R^4$, independently of the others, is halo, alkyl of 1 to 4 carbon atoms, or alkoxy of 1 to 4 carbon atoms or (ii) one of $R^1$, $R^2$, $R^3$, and $R^4$ is —$NHR^5$ and the remaining of $R^1$, $R^2$, $R^3$, and $R^4$ are hydrogen;
$R^5$ is hydrogen or alkyl of 1 to 8 carbon atoms;
$R^6$ is hydrogen, alkyl of 1 to 8 carbon atoms, benzo, chloro, or fluoro;
$R^7$ is m-phenylene or p-phenylene or —$(C_nH_2n)$— in which n has a value of 0 to 4;
each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2$ $X^1CH_2CH_2$— in which $X^1$ is —O—, —S—, or —NH—;
$R^{10}$ is hydrogen, alkyl of to 8 carbon atoms, or phenyl.
Other representative compounds are of formula:

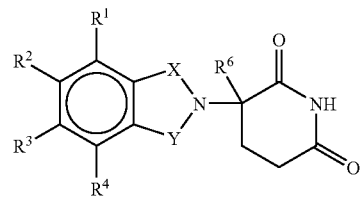

in which
one of X and Y is C═O and the other of X and Y is C═O or $CH_2$;
each of $R^1$, $R^2$, $R^3$, and $R^4$, independently of the others, is halo, alkyl of 1 to 4 carbon atoms, or alkoxy of 1 to 4 carbon atoms or (ii) one of $R^1$, $R^2$, $R^3$, and $R^4$ is nitro or protected amino and the remaining of $R^1$, $R^2$, $R^3$, and $R^4$ are hydrogen; and
$R^6$ is hydrogen, alkyl of 1 to 8 carbon atoms, benzo, chloro, or fluoro.
Other representative compounds are of formula:

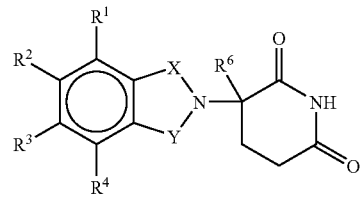

in which:
one of X and Y is C═O and the other of X and Y is C═O or $CH_2$;
(i) each of $R^1$, $R^2$, $R^3$, and $R^4$, independently of the others, is halo, alkyl of 1 to 4 carbon atoms, or alkoxy of 1 to 4 carbon atoms or (ii) one of $R^1$, $R^2$, $R^3$, and $R^4$ is —$NHR^5$ and the remaining of $R^1$, $R^2$, $R^3$, and $R^4$ are hydrogen;
$R^5$ is hydrogen, alkyl of 1 to 8 carbon atoms, or CO—$R^7$—$CH(R^{10})NR^8R^9$ in which each of $R^7$, $R^8$, $R^9$, and $R^{10}$ is as herein defined; and
$R^6$ is alkyl of 1 to 8 carbon atoms, benzo, chloro, or fluoro.
Specific examples of the compounds are of formula:

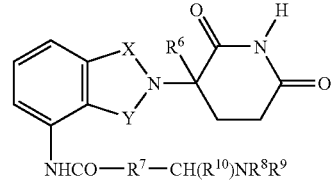

NHCO—$R^7$—$CH(R^{10})NR^8R^9$ in which:
one of X and Y is C═O and the other of X and Y is C═O or $CH_2$;
$R^6$ is hydrogen, alkyl of 1 to 8 carbon atoms, benzyl, chloro, or fluoro;
$R^7$ is m-phenylene, p-phenylene or —$(C_nH_{2n})$— in which n has a value of 0 to 4;

each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2X^1CH_2CH_2$— in which $X^1$ is —O—, —S— or —NH—; and $R^{10}$ is hydrogen, alkyl of 1 to 8 carbon atoms, or phenyl.

The most preferred immunomodulatory compounds of the invention are 4-(amino)-2-(2,6-dioxo(3-piperidyl))-isoindoline-1,3-dione and 3-(4-amino-1-oxo-1,3-dihydro-isoindol-2-yl)-piperidine-2,6-dione. The compounds can be obtained via standard, synthetic methods (see e.g., U.S. Pat. No. 5,635,517, incorporated herein by reference). The compounds are available from Celgene Corporation, Warren, N.J. 4-(Amino)-2-(2,6-dioxo(3-piperidyl))-isoindoline-1,3-dione has the following chemical structure:

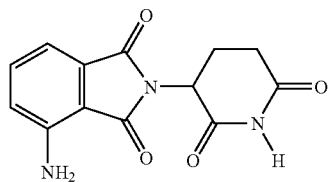 [SMILES: Nc1cccc2c1C(=O)N(C1CCC(=O)NC1=O)C2=O]

The compound 3-(4-amino-1-oxo-1,3-dihydro-isoindol-2-yl)-piperidine-2,6-dione has the following chemical structure:

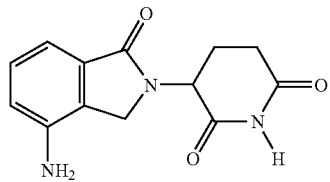 [SMILES: Nc1cccc2c1CN(C1CCC(=O)NC1=O)C2=O]

In another embodiment, specific immunomodulatory compounds of the invention encompass polymorphic forms of 3-(4-amino-1-oxo-1,3 dihydro-isoindol-2-yl)-piperidene-2,6-dione such as Form A, B, C, D, E, F, G and H, disclosed in U.S. provisional application No. 60/499,723 filed on Sep. 4, 2003, and the corresponding U.S. non-provisional application, filed Sep. 3, 2004, both of which are incorporated herein by reference. For example, Form A of 3-(4-amino-1-oxo-1,3 dihydro-isoindol-2-yl)-piperidene-2,6-dione is an unsolvated, crystalline material that can be obtained from non-aqueous solvent systems. Form A has an X-ray powder diffraction pattern comprising significant peaks at approximately 8, 14.5, 16, 17.5, 20.5, 24 and 26 degrees 2θ, and has a differential scanning calorimetry melting temperature maximum of about 270° C. Form A is weakly or not hygroscopic and appears to be the most thermodynamically stable anhydrous polymorph of 3-(4-amino-1-oxo-1,3 dihydro-isoindol-2-yl)-piperidine-2,6-dione discovered thus far.

Form B of 3-(4-amino-1-oxo-1,3 dihydro-isoindol-2-yl)-piperidene-2,6-dione is a hemihydrated, crystalline material that can be obtained from various solvent systems, including, but not limited to, hexane, toluene, and water. Form B has an X-ray powder diffraction pattern comprising significant peaks at approximately 16, 18, 22 and 27 degrees 2θ, and has endotherms from DSC curve of about 146 and 268° C., which are identified dehydration and melting by hot stage microscopy experiments. Interconversion studies show that Form B converts to Form E in aqueous solvent systems, and converts to other forms in acetone and other anhydrous systems.

Form C of 3-(4-amino-1-oxo-1,3 dihydro-isoindol-2-yl)-piperidene-2,6-dione is a hemisolvated crystalline material that can be obtained from solvents such as, but not limited to, acetone. Form C has an X-ray powder diffraction pattern comprising significant peaks at approximately 15.5 and 25 degrees 2θ, and has a differential scanning calorimetry melting temperature maximum of about 269° C. Form C is not hygroscopic below about 85% RH, but can convert to Form B at higher relative humidities.

Form D of 3-(4-amino-1-oxo-1,3 dihydro-isoindol-2-yl)-piperidene-2,6-dione is a crystalline, solvated polymorph prepared from a mixture of acetonitrile and water. Form D has an X-ray powder diffraction pattern comprising significant peaks at approximately 27 and 28 degrees 2θ, and has a differential scanning calorimetry melting temperature maximum of about 270° C. Form D is either weakly or not hygroscopic, but will typically convert to Form B when stressed at higher relative humidities.

Form E of 3-(4-amino-1-oxo-1,3 dihydro-isoindol-2-yl)-piperidene-2,6-dione is a dihydrated, crystalline material that can be obtained by slurrying 3-(4-amino-1-oxo-1,3 dihydro-isoindol-2-yl)-piperidene-2,6-dione in water and by a slow evaporation of 3-(4-amino-1-oxo-1,3 dihydro-isoindol-2-yl)-piperidene-2,6-dione in a solvent system with a ratio of about 9:1 acetone:water. Form E has an X-ray powder diffraction pattern comprising significant peaks at approximately 20, 24.5 and 29 degrees 2θ, and has a differential scanning calorimetry melting temperature maximum of about 269° C. Form E can convert to Form C in an acetone solvent system and to Form G in a THF solvent system. In aqueous solvent systems, Form E appears to be the most stable form. Desolvation experiments performed on Form E show that upon heating at about 125° C. for about five minutes, Form E can convert to Form B. Upon heating at 175° C. for about five minutes, Form B can convert to Form F.

Form F of 3-(4-amino-1-oxo-1,3 dihydro-isoindol-2-yl)-piperidene-2,6-dione is an unsolvated, crystalline material that can be obtained from the dehydration of Form E. Form F has an X-ray powder diffraction pattern comprising significant peaks at approximately 19, 19.5 and 25 degrees 2θ, and has a differential scanning calorimetry melting temperature maximum of about 269° C.

Form G of 3-(4-amino-1-oxo-1,3 dihydro-isoindol-2-yl)-piperidene-2,6-dione is an unsolvated, crystalline material that can be obtained from slurrying forms B and E in a solvent such as, but not limited to, tetrahydrofuran (THF). Form G has an X-ray powder diffraction pattern comprising significant peaks at approximately 21, 23 and 24.5 degrees 2θ, and has a differential scanning calorimetry melting temperature maximum of about 267° C.

Form H of 3-(4-amino-1-oxo-1,3 dihydro-isoindol-2-yl)-piperidene-2,6-dione is a partially hydrated (about 0.25 moles) crystalline material that can be obtained by exposing Form E to 0% relative humidity. Form H has an X-ray powder diffraction pattern comprising significant peaks at approximately 15, 26 and 31 degrees 2θ, and has a differential scanning calorimetry melting temperature maximum of about 269° C.

Other specific immunomodulatory compounds of the invention include, but are not limited to, 1-oxo-2-(2,6-dioxo-3-fluoropiperidin-3-yl) isoindolines and 1,3-dioxo-2-(2,6-dioxo-3-fluoropiperidine-3-yl) isoindolines such as those described in U.S. Pat. Nos. 5,874,448 and 5,955,476, each of which is incorporated herein by reference. Representative compounds are of formula:

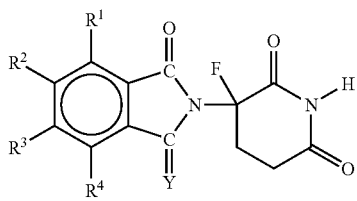

wherein Y is oxygen or $H^2$ and each of $R^1$, $R^2$, $R^3$, and $R^4$, independently of the others, is hydrogen, halo, alkyl of 1 to 4 carbon atoms, alkoxy of 1 to 4 carbon atoms, or amino.

Other specific immunomodulatory compounds of the invention include, but are not limited to, the tetra substituted 2-(2,6-dioxopiperdin-3-yl)-1-oxoisoindolines described in U.S. Pat. No. 5,798,368, which is incorporated herein by reference. Representative compounds are of formula:

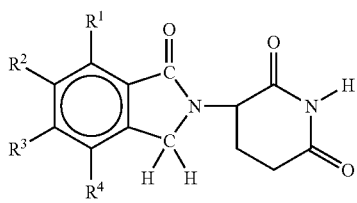

wherein each of $R^1$, $R^2$, $R^3$, and $R^4$, independently of the others, is halo, alkyl of 1 to 4 carbon atoms, or alkoxy of 1 to 4 carbon atoms.

Other specific immunomodulatory compounds of the invention include, but are not limited to, 1-oxo and 1,3-dioxo-2-(2,6-dioxopiperidin-3-yl) isoindolines disclosed in U.S. Pat. No. 6,403,613, which is incorporated herein by reference. Representative compounds are of formula:

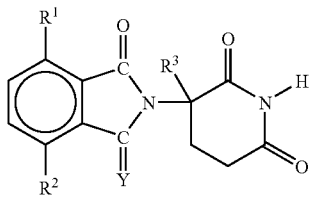

in which
Y is oxygen or $H_2$,
a first of $R^1$ and $R^2$ is halo, alkyl, alkoxy, alkylamino, dialkylamino, cyano, or carbamoyl, the second of $R^1$ and $R^2$, independently of the first, is hydrogen, halo, alkyl, alkoxy, alkylamino, dialkylamino, cyano, or carbamoyl, and
$R^3$ is hydrogen, alkyl, or benzyl.
Specific examples of the compounds are of formula:

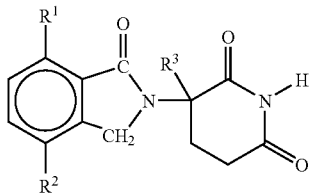

wherein a first of $R^1$ and $R^2$ is halo, alkyl of from 1 to 4 carbon atoms, alkoxy of from 1 to 4 carbon atoms, dialkylamino in which each alkyl is of from 1 to 4 carbon atoms, cyano, or carbamoyl, the second of $R^1$ and $R^2$, independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl, and $R^3$ is hydrogen, alkyl of from 1 to 4 carbon atoms, or benzyl. Specific examples include, but are not limited to, 1-oxo-2-(2,6-dioxopiperidin-3-yl)-4-methylisoindoline.

Other representative compounds are of formula:

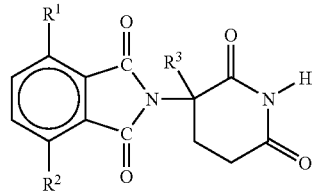

wherein a first of $R^1$ and $R^2$ is halo, alkyl of from 1 to 4 carbon atoms, alkoxy of from 1 to 4 carbon atoms, dialkylamino in which each alkyl is of from 1 to 4 carbon atoms, cyano, or carbamoyl, the second of $R^1$ and $R^2$, independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl, and $R^3$ is hydrogen, alkyl of from 1 to 4 carbon atoms, or benzyl.

Other specific immunomodulatory compounds of the invention include, but are not limited to, 1-oxo and 1,3-dioxoisoindolines substituted in the 4- or 5-position of the indoline ring described in U.S. Pat. No. 6,380,239 and co-pending U.S. application Ser. No. 10/900,270, filed Jul. 28, 2004, which are incorporated herein by reference. Representative compounds are of formula:

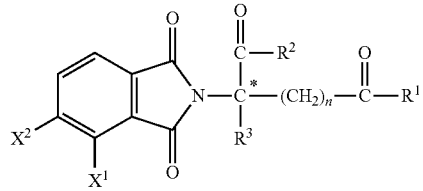

in which the carbon atom designated C* constitutes a center of chirality (when n is not zero and $R^1$ is not the same as $R^2$); one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is hydrogen, alkyl of one to six carbons, halo, or haloalkyl; Z is hydrogen, aryl, alkyl of one to six carbons, formyl, or acyl of one to six carbons; and n has a value of 0, 1, or 2; provided that if $X^1$ is amino, and n is 1 or 2, then $R^1$ and $R^2$ are not both hydroxy; and the salts thereof.

Further representative compounds are of formula:

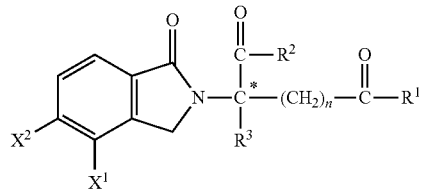

in which the carbon atom designated C* constitutes a center of chirality when n is not zero and $R^1$ is not $R^1$; one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is alkyl of one to six carbons, halo, or hydrogen; Z is hydrogen, aryl or an alkyl or acyl of one to six carbons; and n has a value of 0, 1, or 2.

Specific examples include, but are not limited to, 2-(4-amino-1-oxo-1,3-dihydro-isoindol-2-yl)-4-carbamoyl-butyric acid and 4-(4-amino-1-oxo-1,3-dihydro-isoindol-2-yl)-4-cabamoyl-butyric acid, which have the following structures, respectively, and pharmaceutically acceptable salts, solvates, prodrugs, and stereoisomers thereof:

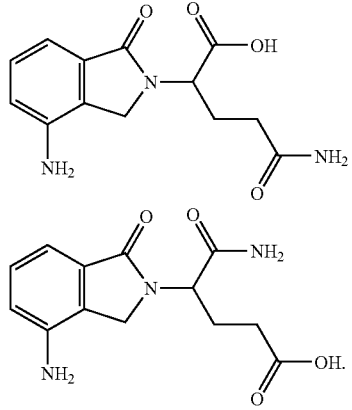

Other representative compounds are of formula:

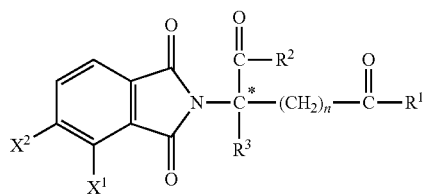

in which the carbon atom designated C* constitutes a center of chirality when n is not zero and $R^1$ is not $R^2$; one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is alkyl of one to six carbons, halo, or hydrogen; Z is hydrogen, aryl, or an alkyl or acyl of one to six carbons; and n has a value of 0, 1, or 2; and the salts thereof.

Specific examples include, but are not limited to, 4-carbamoyl-4-{4-[(furan-2-yl-methyl)-amino]-1,3-dioxo-1,3-dihydro-isoindol-2-yl}-butyric acid, 4-carbamoyl-2-{4[(furan-2-yl-methyl)-amino]-1,3-dioxo-1,3-dihydro-isoindol-2-yl}-butyric acid, 2-{4-[(furan-2-yl-methyl)-amino]-1,3-dioxo-1,3-dihydro-isoindol-2-yl}-4-phenylcarbamoyl-butyric acid, and 2-{4-[(furan-2-yl-methyl)-amino]-1,3-dioxo-1,3-dihydro-isoindol-2-yl}-pentanedioic acid, which have the following structures, respectively, and pharmaceutically acceptablesalts, solvate, prodrugs, and stereoisomers thereof:

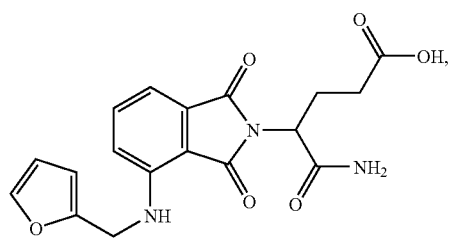

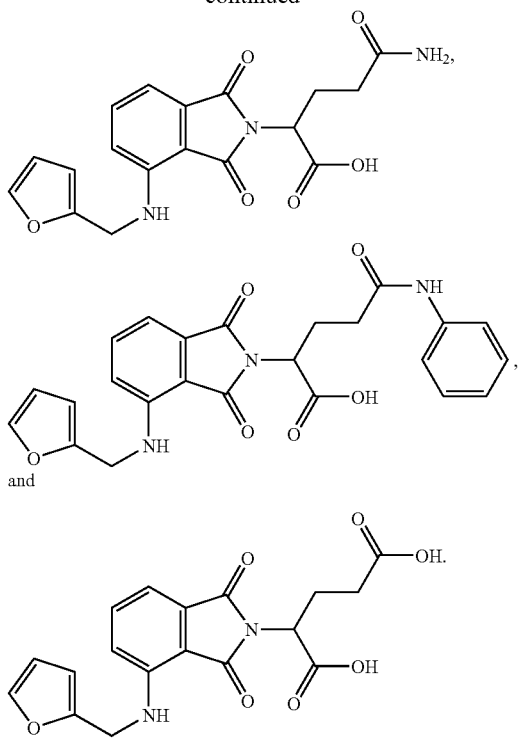

Other specific examples of the compounds are of formula:

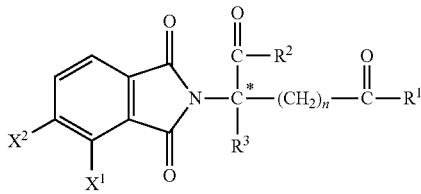

wherein one of $X^1$ and $X^2$ is nitro, or NH—Z, and the other of $X^1$ or $X^2$ is hydrogen;

each of $R^1$ and $R^2$, independent of the other, is hydroxy or NH—Z;

$R^3$ is alkyl of one to six carbons, halo, or hydrogen;

Z is hydrogen, phenyl, an acyl of one to six carbons, or an alkyl of one to six carbons; and n has a value of 0, 1, or 2;

provided that if one of $X^1$ and $X^2$ is nitro, and n is 1 or 2, then $R^1$ and $R^2$ are other than hydroxy; and if —$COR^2$ and —$(CH_2)_nCOR^1$ are different, the carbon atom designated C* constitutes a center of chirality. Other representative compounds are of formula:

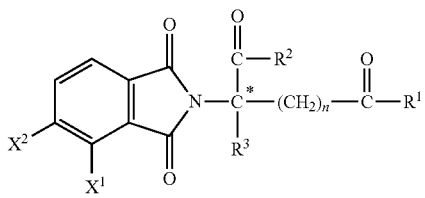

wherein one of $X^1$ and $X^2$ is alkyl of one to six carbons;
each of $R^1$ and $R^2$, independent of the other, is hydroxy or NH—Z;

R³ is alkyl of one to six carbons, halo, or hydrogen;

Z is hydrogen, phenyl, an acyl of one to six carbons, or an alkyl of one to six carbons; and n has a value of 0, 1, or 2; and if —COR² and —(CH₂)ₙCOR¹ are different, the carbon atom designated C* constitutes a center of chirality.

Still other specific immunomodulatory compounds of the invention include, but are not limited to, isoindoline-1-one and isoindoline-1,3-dione substituted in the 2-position with 2,6-dioxo-3-hydroxypiperidin-5-yl described in U.S. Pat. No. 6,458,810, which is incorporated herein by reference. Representative compounds are of formula:

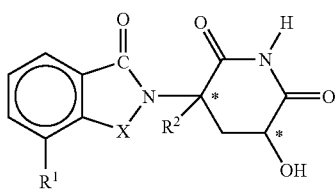

wherein:

the carbon atoms designated * constitute centers of chirality;

X is —C(O)— or —CH₂—;

R¹ is alkyl of 1 to 8 carbon atoms or —NHR³;

R² is hydrogen, alkyl of 1 to 8 carbon atoms, or halogen; and

R³ is hydrogen, alkyl of 1 to 8 carbon atoms, unsubstituted or substituted with alkoxy of 1 to 8 carbon atoms, halo, amino, or alkylamino of 1 to 4 carbon atoms, cycloalkyl of 3 to 18 carbon atoms, phenyl, unsubstituted or substituted with alkyl of 1 to 8 carbon atoms, alkoxy of 1 to 8 carbon atoms, halo, amino, or alkylamino of 1 to 4 carbon atoms, benzyl, unsubstituted or substituted with alkyl of 1 to 8 carbon atoms, alkoxy of 1 to 8 carbon atoms, halo, amino, or alkylamino of 1 to 4 carbon atoms, or —COR⁴ in which R⁴ is hydrogen, alkyl of 1 to 8 carbon atoms, unsubstituted or substituted with alkoxy of 1 to 8 carbon atoms, halo, amino, or alkylamino of 1 to 4 carbon atoms, cycloalkyl of 3 to 18 carbon atoms, phenyl, unsubstituted or substituted with alkyl of 1 to 8 carbon atoms, alkoxy of 1 to 8 carbon atoms, halo, amino, or alkylamino of 1 to 4 carbon atoms, or benzyl, unsubstituted or substituted with alkyl of 1 to 8 carbon atoms, alkoxy of 1 to 8 carbon atoms, halo, amino, or alkylamino of 1 to 4 carbon atoms.

Compounds of the invention can either be commercially purchased or prepared according to the methods described in the patents or patent publications disclosed herein. Further, optically pure compounds can be asymmetrically synthesized or resolved using known resolving agents or chiral columns as well as other standard synthetic organic chemistry techniques.

Various immunomodulatory compounds of the invention contain one or more chiral centers, and can exist as racemic mixtures of enantiomers or mixtures of diastereomers. This invention encompasses the use of stereomerically pure forms of such compounds, as well as the use of mixtures of those forms. For example, mixtures comprising equal or unequal amounts of the enantiomers of a particular immunomodulatory compounds of the invention may be used in methods and compositions of the invention. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, N.Y., 1962); and Wilen, S. H., *Tables of Resolving Agents and Optical Resolutions* p. 268 (E. L. Eliel, Ed., Univ. of Notre Dame Press, Notre Dame, Ind., 1972).

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.3 Second Active Agents

Immunomodulatory compounds can be combined with other pharmacologically active compounds ("second active agents") in methods of the invention. It is believed that certain combinations work synergistically in the treatment, prevention and/or management of immunodeficiency disorders. Immunomodulatory compounds can also work to alleviate adverse effects associated with certain second active agents, and some second active agents can be used to alleviate adverse effects associated with immunomodulatory compounds.

One or more second active ingredients or agents can be used in the methods of the invention together with an immunomodulatory compound. Second active agents can be large molecules (e.g., proteins) or small molecules (e.g., synthetic inorganic, organometallic, or organic molecules).

This invention also encompasses the use of native, naturally occurring, and recombinant proteins. The invention further encompasses mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101(2001).

In one embodiment of the invention, the large molecule active agent reduces, eliminates, or prevents an adverse effect associated with the administration of an immunomodulatory compound. Depending on the particular immunomodulatory compound and the disease or disorder being treated, adverse effects can include, but are not limited to, drowsiness and somnolence, dizziness and orthostatic hypotension, neutropenia, infections that result from neutropenia, increased HIV-viral load, bradycardia, Stevens-Johnson Syndrome and toxic epidermal necrolysis, and seizures (e.g., grand mal convulsions).

Second active agents that are small molecules can also be used to alleviate adverse effects associated with the administration of an immunomodulatory compound. However, like some large molecules, many are believed to be capable of providing a synergistic effect when administered with (e.g., before, after or simultaneously) an immunomodulatory compound.

Specific second active agents include, but are not limited to: antibiotics (therapeutic or prophylactic) such as, but not limited to, ampicillin, tetracycline, penicillin, cephalosporins, streptomycin, kanamycin, and erythromycin; antivirals such as, but not limited to, amantadine, rimantadine, acyclovir, and ribavirin; immunoglobulin; plasma; immunologic enhancing drugs such as, but not limited to, levamisole and isoprinosine; biologics such as, but not limited to, gamma-globulin, transfer factor, interleukins, and interferons; hormones such as, but not limited to, thymic; and other immunologic agents such as, but not limited to, B cell stimulators (e.g., BAFF/BlyS), cytokines (e.g., IL-2, IL-4, and IL-5), growth factors (e.g., TGF-β), antibodies (e.g., anti-CD40 and IgM), oligonucleotides containing unmethylated CpG motifs (e.g., TCGTCGTTTTGTCGTTTTGTCGTT), and vaccines (e.g., viral and tumor peptide vaccines).

In another embodiment, methods of this invention can be used in combination with other methods used for the treatment, prevention, and/or management of an immunodeficiency disease or disorder. Examples of other methods include, but not limited to, stem cell transplantation, enzyme replacement therapy using, for example, bovine adenosine deaminase conjugated to polyethylene glycol (PEG-ADA), fetal thymus transplant, cultured neonatal thymus transplant, thymic epithelial cell transplant, and fetal liver transplant.

5.4 Methods of Treatments and Prevention

Methods of this invention encompass methods of treating, preventing and/or managing various immunodeficiency diseases or disorders. Examples of such diseases or disorders include, but are not limited to, adenosine deaminase deficiency, antibody deficiency with normal or elevated Igs, ataxia-tenlangiectasia, bare lymphocyte syndrome, common variable immunodeficiency, DiGeorge syndrome, Ig deficiency with hyper-IgM, Ig heavy chain deletions, IgA deficiency, immunodeficiency with thymoma, reticular dysgenesis, Nezelof syndrome, selective IgG subclass deficiency, transient hypogammaglobulinemia of infancy, Wistcott-Aldrich syndrome, X-linked agammaglobulinemia, and X-linked severe combined immunodeficiency.

Methods encompassed by this invention comprise administering one or more immunomodulatory compound of the invention, or a pharmaceutically acceptable salt, solvate, stereoisomer, or prodrug thereof, to a patient (e.g., a human) suffering, or likely to suffer, from an immunodeficiency disease or disorder.

In one embodiment of the invention, an immunomodulatory compound of the invention can be administered orally and in single or divided daily doses in an amount of from about 0.10 to about 150 mg/day. In a particular embodiment, 4-(amino)-2-(2,6-dioxo(3-piperidyl))-isoindoline-1,3-dione may be administered in an amount of from about 0.1 to about 1 mg per day, or alternatively from about 0.1 to about 5 mg every other day. In a particular embodiment, 3-(4-amino-1-oxo-1,3-dihydro-isoindol-2-yl)-piperidine-2,6-dione may be administered in an amount of from about 1 to about 25 mg per day, or alternatively from about 10 to about 50 mg every other day. In another embodiment, 3-(4-amino-1-oxo-1,3-dihydro-isoindol-2-yl)-piperidine-2,6-dione may be administered in an amount of about 50 mg per day. In another embodiment, 3-(4-amino-1-oxo-1,3-dihydro-isoindol-2-yl)-piperidine-2,6-dione may be administered in an amount of about 25 mg per day. In another embodiment, 3-(4-amino-1-oxo-1,3-dihydro-isoindol-2-yl)-piperidine-2,6-dione may be administered in an amount of about 10 mg per day.

It is believed that the immunomodulatory compounds of this invention are effective in boosting humoral immunity in a patient. Therefore, in another embodiment, this invention encompasses methods of enhancing an immune response to an immunogen, comprising administering a therapeutically or prophylactically effective amount of an immunomodulatory compound of the invention, or a pharmaceutically acceptable salt, solvate, stereoisomer, or prodrug thereof, to a patient in need of such enhancement. The immunomodulatory compound may be administered prior to, during, or subsequent to the patient's exposure to the immunogen.

In a particular embodiment, the immunomodulatory compounds of this invention may be used to enhance the effect of vaccines such as, but not limited to, vaccines for pathogenic disorders, cancer, and autoimmune diseases. One of the goals of vaccines is to mount an immune response to an immunogen, and thereby forming a population of memory B-cells (and T-cells) that have affinity for the particular immunogen. Without being limited by a particular theory, it is believed that since immunomodulatory compounds used in the invention are shown to enhance the level, proliferation, and activation of B-cell TLR 9, the formation of memory cells may be enhanced, and immunologic protection against the immunogen can be improved. Therefore, this invention also encompasses a method of enhancing the immune response to an immunogen in a patient, comprising administering to a patient in need of such enhancement an immunomodulatory compound and a vaccine comprising the immunogen. The immunomodulatory compound can be administered prior to, simultaneously with, and subsequent to the administration of the vaccine.

Suitable vaccines that can be used with immunomodulatory compounds include, but are not limited to, those comprising antigens from an animal, a plant, a bacteria, a protozoan, a parasite, a virus or a combination thereof. The antigenic or immunogenic agent may be any viral peptide, protein, polypeptide, or a fragment thereof derived from a virus including, but not limited to, RSV-viral proteins, e.g., RSV F glycoprotein, RSV G glycoprotein, influenza viral proteins, e.g., influenza virus neuramimidase, influenza virus hemagglutinin, herpes simplex viral protein, e.g., herpes simplex virus glycoprotein including for example, gB, gC, gD, and gE. The antigenic or immunogenic agent for use in the compositions of the invention may be an antigen of a pathogenic virus such as, an antigen of adenovirdiae (e.g., mastadenovirus and aviadenovirus), herpesviridae (e.g., herpes simplex virus 1, herpes simplex virus 2, herpes simplex virus 5, and herpes simplex virus 6), leviviridae (e.g., levivirus, enterobacteria phase MS2, allolevirus), poxyridae (e.g., chordopoxyirinae, parapoxvirus, avipoxvirus, capripoxvirus, leporipoxvirus, suipoxvirus, molluscipoxvirus, and entomopoxyirinae), papovaviridae (e.g., polyomavirus and papillomavirus), paramyxoviridae (e.g., paramyxovirus, parainfluenza virus 1, mobillivirus (e.g., measles virus), rubulavirus (e.g., mumps virus), pneumonovirinae (e.g., pneumovirus, human respiratory syncytial virus), metapneumovirus (e.g., avian pneumovirus and human metapneumovirus), picornaviridae (e.g., enterovirus, rhinovirus, hepatovirus (e.g., human hepatitis A virus), cardiovirus, and apthovirus), reoviridae (e.g., orthoreovirus, orbivirus, rotavirus, cypovirus, fijivirus, phytoreovirus, and oryzavirus), retroviridae (e.g., mammalian type B retroviruses, mammalian type C retroviruses, avian type C retroviruses, type D retrovirus group, BLV-HTLV retroviruses), lentivirus (e.g human immunodeficiency virus 1 and human immunodeficiency virus 2), spumavirus, flaviviridae (e.g., hepatitis C virus), hepadnaviridae (e.g., hepatitis B virus), togaviridae (e.g., alphavirus (e.g., sindbis virus) and rubivirus (e.g., rubella virus), rhabdoviridae (e.g., vesiculovirus, lyssavirus, ephemerovirus, cytorhabdovirus, and necleorhabdovirus), arenaviridae (e.g., arenavirus, lymphocytic choriomeningitis virus, Ippy virus, and lassa virus), and coronaviridae (e.g., coronavirus and torovirus).

In one embodiment, the vaccines may be those comprising a cancer or tumor antigen including but not limited to, KS 1/4 pan-carcinoma antigen, ovarian carcinoma antigen (CA125), prostatic acid phosphate, prostate specific antigen, melanoma-associated antigen p97, melanoma antigen gp75, high molecular weight melanoma antigen (HMW-MAA), prostate specific membrane antigen, carcinoembryonic antigen (CEA), polymorphic epithelial mucin antigen, human milk fat globule antigen, colorectal tumor-associated antigens such as: CEA, TAG-72, CO17-1A; GICA 19-9, CTA-1 and LEA, Burkitt's lymphoma antigen-38.13, CD 19, human B-lymphoma antigen-CD20, CD33, melanoma specific antigens such as ganglioside GD2, ganglioside GD3, ganglioside GM2, ganglioside GM3, tumor-specific transplantation type of cell-surface antigen (TSTA) such as virally-induced tumor antigens including T-antigen DNA tumor viruses and Envelope antigens of RNA tumor viruses, oncofetal antigen-alpha-fetoprotein such as CEA of colon, bladder tumor oncofetal antigen, differentiation antigen such as human lung carcinoma antigen L6, L20, antigens of fibrosarcoma, human leukemia T cell antigen-Gp37, neoglycoprotein, sphingolipids, breast cancer antigen such as EGFR (Epidermal growth factor receptor), HER$^2$ antigen (p185$^{HER2}$), polymorphic epithelial mucin (PEM), malignant human lymphocyte antigen-APO-1, differentiation antigen such as I antigen found in fetal erythrocytes, primary endoderm, I antigen found in adult erythrocytes, preimplantation embryos, I(Ma) found in gastric adenocarcinomas, M18, M39 found in breast epithelium, SSEA-1 found in myeloid cells, VEP8, VEP9, Myl, VIM-D5, $D_1$56-22 found in colorectal cancer, TRA-1-85 (blood group H), C14 found in colonic adenocarcinoma, F3 found in lung adenocarcinoma, AH6 found in gastric cancer, Y hapten, Le$^y$ found in embryonal carcinoma cells, TL5 (blood group A), EGF receptor found in A431 cells, $E_1$ series (blood group B) found in pancreatic cancer, FC10.2 found in embryonal carcinoma cells, gastric adenocarcinoma antigen, CO-514 (blood group Le$^a$) found in Adenocarcinoma, NS-10 found in adenocarcinomas, CO-43 (blood group Le$^b$), G49 found in EGF receptor of A431 cells, MH2 (blood group ALe$^b$/Le$^y$) found in colonic adenocarcinoma, 19.9 found in colon cancer, gastric cancer mucins, $T_5A_7$ found in myeloid cells, $R_{24}$ found in melanoma, 4.2, GD3, D1.1, OFA-1, $G_{M2}$, OFA-2, GD2, and M1:22:25:8 found in embryonal carcinoma cells, and SSEA-3 and SSEA-4 found in 4 to 8-cell stage embryos, and T cell receptor derived peptide from a Cutaneous T cell Lymphoma.

The immunogen for use in the vaccine may be any substance that under appropriate conditions results in an immune response in a subject, including, but not limited to, polypeptides, peptides, proteins, glycoproteins, lipids, nucleic acids, and polysaccharides. The concentration of immunogen in the vaccine may be determined using standard methods known to one skilled in the art and depends on the potency and nature of the immunogen.

Patients in need of humoral immunity boost can be determined based on variety of factors, including, but not limited to, demographics, genetic factors, and work environment. Persons who dwell in or travel to an area where high level exposure to pathogens is likely are one example of such patients. Persons who have family history of genetically descended immune disorder are another example. Furthermore, persons who are typically exposed to high level of pathogens (e.g., health workers) are yet another example of such patients.

As used herein, and unless otherwise specified, the term "enhancing" or "enhance," when used in connection with immune response, means that when an antigenic or immunogenic agent is administered to a subject who has been or is being treated with an immunomodulatory compound, there is an increased antibody formation, as compared to a subject to which same amount of the antigenic or immunogenic agent alone is administered, as determined by any conventional methods of antibody level determination known in the art, for example, nephelometry, immunoelectrophoresis, radioimmunoassay, and ELISA. In some embodiments, when methods of this invention are used, antibody formation is increased by about 5%, 10%, 20%, 50%, or 100% or more, as compared to the antibody formation obtained when such methods are not used.

As used herein, and unless otherwise specified, the term "immunogen" means any foreign objects that can trigger an immune response, i.e., formation of antibodies, in a subject. Immunogens include, but are not limited to, antigens from an animal, a plant, a bacteria, a protozoan, a parasite, a virus or a combination thereof. Immunogens may be any substance that results in an immune response in a subject, including, but not limited to, polypeptides, peptides, proteins, glycoproteins, and polysaccharides.

5.4.1 Combination Therapy with a Second Active Agent or Therapy

Specific methods of the invention comprise administering an immunomodulatory compound of the invention, or a pharmaceutically acceptable salt, solvate, stereoisomer, or prodrug thereof, in combination with one or more second active agents or other therapies. Examples of immunomodulatory compounds of the invention are disclosed herein (see, e.g., section 5.2). Examples of second active agents and other therapies are also disclosed herein (see, e.g., section 5.3).

Administration of the immunomodulatory compounds and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. A particular route of administration for an immunomodulatory compound of the invention is oral. Particular routes of administration for the second active agents or ingredients of the invention are known to those of ordinary skill in the art. See, e.g., *The Merck Manual*, 1023-1041 (17$^{th}$ ed., 1999).

The amount of second active agent administered can be determined based on the specific agent used, the type of disease being treated or managed, the severity and stage of disease, and the amount(s) of immunomodulatory compounds of the invention and any optional additional active agents concurrently administered to the patient. Those of ordinary skill in the art can determine the specific amounts according to conventional procedures known in the art. In the beginning, one can start from the amount of the second active agent that is conventionally used in the therapies, and adjust the amount according to the factors described above. See, e.g., *Physician's Desk Reference* (56$^{th}$ Ed., 2004).

In one embodiment of the invention, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount(s) of immunomodulatory compounds of the invention and any optional additional active agents concurrently administered to the patient.

In one embodiment, an immunomodulatory compound can be administered in an amount of from about 0.1 to about 150 mg, and preferably from about 1 to about 25 mg, more preferably from about 2 to about 10 mg orally and daily alone, or in combination with a second active agent disclosed herein (see, e.g., section 5.3), prior to, during, or after the use of conventional therapy.

5.4.2 Cycling Therapy

In certain embodiments, the prophylactic or therapeutic agents of the invention are cyclically administered to a patient. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

Consequently, in one specific embodiment of the invention, an immunomodulatory compound of the invention is administered daily in a single or divided doses in a four to six week cycle with a rest period of about a week or two weeks. The invention further allows the frequency, number, and length of dosing cycles to be increased. Thus, another specific embodiment of the invention encompasses the administration of an immunomodulatory compound of the invention for more cycles than are typical when it is administered alone.

In yet another specific embodiment of the invention, an immunomodulatory compound of the invention is administered for a greater number of cycles that would typically cause dose-limiting toxicity in a patient to whom a second active ingredient is not also being administered.

In one embodiment, an immunomodulatory compound of the invention is administered daily and continuously for three or four weeks at a dose of from about 0.1 to about 150 mg/d followed by a break of one or two weeks. 4-(Amino)-2-(2,6-dioxo(3-piperidyl))-isoindoline-1,3-dione is preferably administered daily and continuously at an initial dose of 0.1 to 5 mg/d with dose escalation (every week) by 1 to 10 mg/d to a maximum dose of 50 mg/d for as long as therapy is tolerated. In a particular embodiment, 3-(4-amino-1-oxo-1,3-dihydro-isoindol-2-yl)-piperidine-2,6-dione is administered in an amount of about 1, 5, 10, or 25 mg/day, preferably in an amount of about 10 mg/day for three to four weeks, followed by one week or two weeks of rest in a four or six week cycle.

In one embodiment of the invention, an immunomodulatory compound of the invention and a second active ingredient are administered orally, with administration of an immunomodulatory compound of the invention occurring 30 to 60 minutes prior to a second active ingredient, during a cycle of four to six weeks. In another embodiment of the invention, the combination of an immunomodulatory compound of the invention and a second active ingredient is administered by intravenous infusion over about 90 minutes every cycle. In a specific embodiment, one cycle comprises the administration of from about 1 to about 25 mg/day of 3-(4-amino-1-oxo-1,3-dihydro-isoindol-2-yl)-piperidine -2,6-dione and from about 50 to about 200 mg/m$^2$/day of a second active ingredient daily for three to four weeks and then one or two weeks of rest. In another specific embodiment, each cycle comprises the administration of from about 5 to about 10 mg/day of 4-(amino)-2-(2,6-dioxo(3-piperidyl))-isoindoline-1,3-dione and from about 50 to about 200 mg/m$^2$/day of a second active ingredient for 3 to 4 weeks followed by one or two weeks of rest. Typically, the number of cycles during which the combinatorial treatment is administered to a patient will be from about one to about 24 cycles, more typically from about two to about 16 cycles, and even more typically from about four to about three cycles.

5.5 Pharmaceutical Compositions and Dosage Forms

Pharmaceutical compositions can be used in the preparation of individual, single unit dosage forms. Pharmaceutical compositions and dosage forms of the invention comprise an immunomodulatory compound of the invention, or a pharmaceutically acceptable salt, solvate, stereoisomer, or prodrug thereof, and a second active agent. Pharmaceutical compositions and dosage forms of the invention can further comprise one or more excipients.

Pharmaceutical compositions and dosage forms of the invention can also comprise one or more additional active ingredients. Consequently, pharmaceutical compositions and dosage forms of the invention comprise the active ingredients disclosed herein (e.g., an immunomodulatory compound and a second active agent). Examples of optional second, or additional, active ingredients are disclosed herein (see, e.g., section 5.3).

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, this invention encompasses pharmaceutical compositions and dosage forms that contain little, if any, lactose other mono- or disaccharides. As used herein, the term "lactose-free" means that the amount of lactose present, if any, is insufficient to substantially increase the degradation rate of an active ingredient.

Lactose-free compositions of the invention can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. Particular lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise an immunomodulatory compound of the invention or a pharmaceutically acceptable salt, solvate, stereoisomer, or prodrug thereof in an amount of from about 0.10 to about 150 mg. Typical dosage forms comprise an immunomodulatory compound of the invention or a pharmaceutically acceptable salt, solvate, stereoisomer, or prodrug thereof in an amount of about 0.1, 1, 2, 5, 7.5, 10, 12.5, 15,17.5, 20, 25, 50, 100, 150 or 200 mg. In a particular embodiment, a dosage form comprises 4-(amino)-2-(2,6-dioxo(3-piperidyl))-isoindoline-1,3-dione in an amount of about 1, 2, 5, 10, 25 or 50 mg. In a specific embodiment, a dosage form comprises 3-(4-amino-1-oxo-1,3-dihydro-isoindol-2-yl)-piperidine-2,6-dione in an amount of about 5, 10, 25 or 50 mg. Typical dosage forms comprise the second active ingredient in an amount of 1 to about 1000 mg, from about 5 to about 500 mg, from about 10 to about 350 mg, or from about 50 to about 200 mg. Of course, the specific amount of the agent will depend on the specific agent used, the type of disease or disorder being treated or managed, and the amount(s) of an immunomodulatory compound of the invention and any optional additional active agents concurrently administered to the patient.

5.5.1 Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms of the invention are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W. R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A particular solid oral dosage form of the invention comprises an immunomodulatory compound of the invention, anhydrous lactose, microcrystalline cellulose, polyvinylpyrrolidone, stearic acid, colloidal anhydrous silica, and gelatin.

5.5.2 Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

5.5.3 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention. For example, cyclodextrin and its derivatives can be used to increase the solubility of an immunomodulatory compound of the invention and its derivatives. See, e.g., U.S. Pat. No. 5,134,127, which is incorporated herein by reference.

5.5.4 Topical and Mucosal Dosage Forms

Topical and mucosal dosage forms of the invention include, but are not limited to, sprays, aerosols, solutions, emulsions, suspensions, eye drops or other ophthalmic preparations, or other forms known to one of skill in the art. See, e.g., *Remington's Pharmaceutical Sciences*, 16$^{th}$ and 18$^{th}$ eds., Mack Publishing, Easton Pa. (1980 & 1990); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences*, 16$^{th}$ and 18$^{th}$ eds., Mack Publishing, Easton Pa. (1980 & 1990).

The pH of a pharmaceutical composition or dosage form may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

5.5.5 Kits

Typically, active ingredients of the invention are preferably not administered to a patient at the same time or by the same route of administration. This invention therefore encompasses kits which, when used by the medical practitioner, can simplify the administration of appropriate amounts of active ingredients to a patient.

A typical kit of the invention comprises a dosage form of an immunomodulatory compound of the invention, or a pharmaceutically acceptable salt, solvate, stereoisomer, or prodrug thereof. Kits encompassed by this invention can further comprise additional active ingredients. Examples of the additional active ingredients include, but are not limited to, those disclosed herein (see, e.g., section 5.3).

Kits of the invention can further comprise devices that are used to administer the active ingredients. Examples of such devices include, but are not limited to, syringes, drip bags, patches, and inhalers.

Kits of the invention can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

6. EXAMPLES

Certain embodiments of the invention are illustrated by the following non-limiting examples.

6.1 Materials and Methods 6.1.1 Materials

Buffy coat (50 ml) from healthy donor was obtained from San Diego Blood Bank. Anti-CD40 (#5555587), FITC conjugated anti human CD69 (#5555530), FITC conjugated anti human CD40 (#555588), PE conjugated anti human CD80 (#557227), PerCP-Cy5.5 conjugated anti human HLA-DR (#552764) CD40 ligand (CD154, #555698) were purchased from BD Pharmingen. LPS from *E. coli* (#L6529,) was purchased from Sigma. Recombinant human IL-4 (#200-04) was purchased from Pepro Tech. Goat anti-human IgM (Fc5u fragment, #109-006-129) was purchased from Jackson Immuno Research, Lab Inc. Cell proliferation ELISA (BrdU, #1-647-229) was purchased from Roche Applied Science. PE anti human TLR 9 (#12-9099, clone # eB72-1665) was purchased from eBioscience. Phospho-STAT 6 (#9361) was purchased from Cell Signaling.

6.1.2 Purification of HPBMCS and Isolation of CD19$^+$ Cells

Human buffy coat (50 ml) was diluted with 50 ml sterile PBS (Ca$^{++}$, Mg$^{++}$ free), and mixed gently. A 25 ml aliquot of diluted buffy coat was transferred to each 50 ml centrifuge tube, and Histopaque-1077 (14 ml, #1077-1, Sigma) was gently layered into the bottom of the tube. The sample was centrifuged at 2,000 rpm for 30 min at room temperature. The interface containing mononuclear cells was transferred into 50 ml centrifuge tube, and washed once with PBS (1200 rpm, 5 min). The supernatant was discarded. Cell pellet was resuspended in Miltenyi buffer. Anti-CD19$^+$ microbeads were added to the suspension (10$^7$ cells in 80 μl of buffer, 20 μl antibody beads for 10$^7$ cells) and incubated for 15 min at 4° C. Cell pellet was washed once and resuspended in 1 ml Miltenyi buffer. The cell suspension was added to the magnetic column, washed with 10 ml Miltenyi buffer in the column. CD19$^+$ cells are released by 1 ml Miltenyi Buffer without magnetic field. CD19$^+$ cells were washed twice with RPMI complete medium. B cells (2×10$^5$) were plated in 96 well plate.

6.1.3 B Cell Stimulation with Anti-IGM, Anti CD40, LPS, BAFF, and IL-4

B cells were pretreated with 1,3-dioxo-(2,6-dioxopiperidin-3-yl)-4-aminoisoindoline or 1-oxo-(2,6-dioxopiperidin-3-yl)-4-aminoisoindoline at the concentrations of 60 μM, 6 μM, 0.6 μM, 0.06 μM, 0.006 μM, and 0.0006 μM for 30 min, then were added 2 μg/ml of anti-IgM, 2 μg/ml of anti CD40, 40 ng/ml IL-4, 100 ng/ml of recombinant BAFF, and/or 0.5 μg/ml of LPS. B cells were typically treated with the immunomodulatory compound alone or in presence of one or more of above stimuli for 3 days. Stimulated B cells with or without the treatment with immunomodulatory compound were used for cell proliferation assay and cytokines analysis.

6.1.4 IgE Elisa

Human PBMCs ($1 \times 10^6$/ml) were treated with immunomodulatory compounds in presence of anti-CD40 (2 ug/ml) and IL-4 (40 ng/ml) for three weeks. Fifty microliter of supernatant was used for IgE ELISA, following the manufacturer's instruction. The absorbance was read by ELISA reader at OD=450 nm.

6.1.5 Western Blotting

CD-19 B cells ($2 \times 10^6$/ml) were pretreated with 1,3-dioxo-(2,6-dioxopiperidin-3-yl)-4-aminoisoindoline at 10 μM and 1 μM for 30 minutes. IL-4 (100 ng/ml) was added to cell suspension for 30 minutes, and the cell pellet was washed once by PBS and lysed with 50 μl of the sample buffer. Cell lysates were heated at 100° C. for 5 minutes, and 20 μl of cell lysates were loaded to 4-20% Tris-glycine SDS-PAGE (Invitrogen). The transferred membrane was blotted with 1: 1000 anti-phopho STAT6 antibody (Cell signaling) for overnight at 4° C. prior to secondary HRP conjugated anti rabbit antibody. The signal of the membrane was developed by ECL kit, following the manufacturer's instructions.

6.2 FACS Analysis of CD80, CD40 and HLA-DR Expression

B cells were treated with 1 μM 1,3-dioxo-(2,6-dioxopiperidin-3-yl)-4-aminoisoindoline in presence of LPS; CD40 ligand and IL-4; or BAFF for 3 days. The suspension of B cells was washed by PBS once, and incubated with FITC conjugated anti human CD40, PE conjugated anti human CD80, or PerCP-Cy5.5 conjugated anti human HLA-DR for 30 min in the dark. B cells were subject to FACS analysis using BD FACSAria (BD biosciences).

Figure 1A:
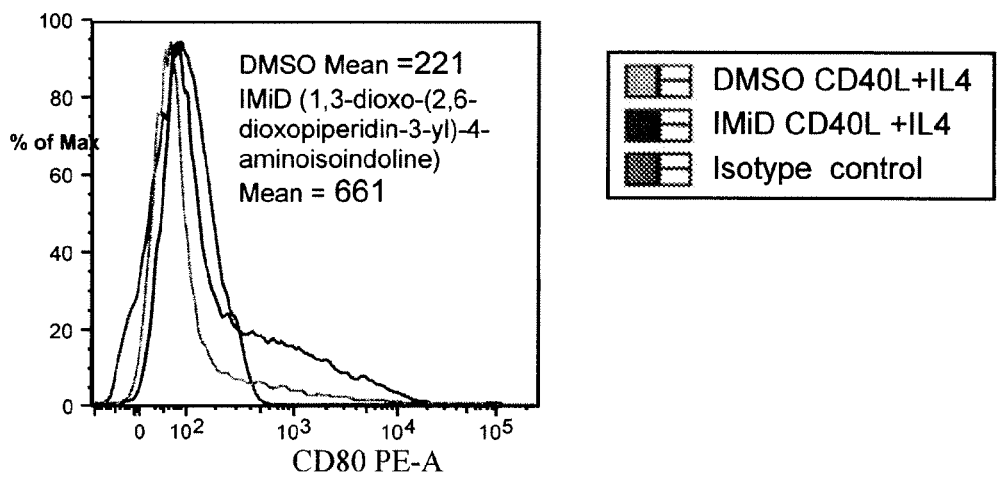
FIG. 1A shows the results from a flow cytometric analysis illustrating the up-regulation of CD80 expression by an immunomodulatory compound on normal B cells treated with CD40L and IL-4.
Figure 1B:
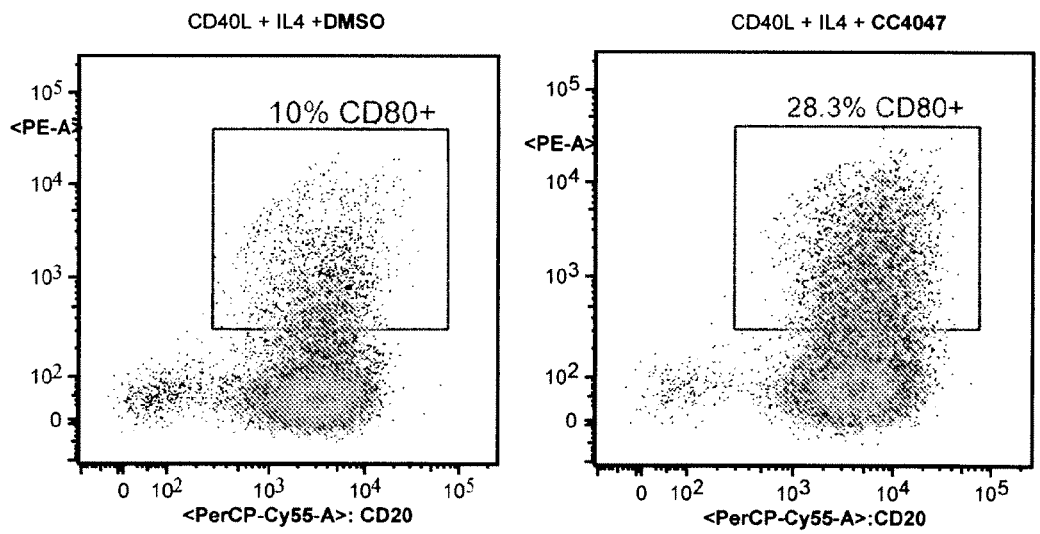
FIG. 1B illustrates the increase in number of B cells expressing CD80 when treated by an immunomodulatory compound.

CD80, CD40 and HLA-DR are molecular markers of B cell activation. As shown in FIG. 1A, normal B cells treated with 1,3-dioxo-(2,6-dioxopiperidin-3-yl)-4-aminoisoindoline in the presence of CD40 ligand and IL-4 exhibited an increased CD80 expression. Moreover, as shown in FIG. 1B, the number of B cells expressing CD80 were also increased when the cells were treated with 1,3-dioxo-(2,6-dioxopiperidin-3-yl)-4-aminoisoindoline. CD40 (FIG. 2A) and HLA-DR expressions were also upregulated by 1,3-dioxo-(2,6-dioxopiperidin-3-yl)-4-aminoisoindoline in B cells treated with BAFF or LPS. These results show that immunomodulatory compound of the invention can stimulate B cell activation.

6.3 FACS Analysis of CD69 expression

B cells were treated with 1,3-dioxo-(2,6-dioxopiperidin-3-yl)-4-aminoisoindoline (FIG. 3A) or 1-oxo-(2,6-dioxopiperidin-3-yl)-4-aminoisoindoline (FIG. 3B) in presence of anti IgM, anti CD40 and IL-4 for 3 days. The suspension of B cells was washed by PBS once, and incubated with FITC conjugated anti human CD69 for 30 min in the dark. B cells were subject to FACS analysis using flow cytometer (EPICS XL-MCL, Beckman Coulter Company).

CD69 is another molecular marker for B cell activation. As shown in FIGS. 3A and 3B, both 1,3-dioxo-(2,6-dioxopiperidin-3-yl)-4-aminoisoindoline and 1-oxo-(2,6-dioxopiperidin-3-yl)-4-aminoisoindoline dose-dependently enhanced CD69 expression in CD 19+B cells treated with anti human IgM, anti human CD40, and recombinant human IL-4. These results show that immunomodulatory compounds of the invention can enhance B cell activation.

6.4 Effects of IMiDs on TNFα Expression

TNFα levels in 1,3-dioxo-(2,6-dioxopiperidin-3-yl)-4-aminoisoindoline or 1-oxo-(2,6-dioxopiperidin-3-yl)-4-aminoisoindoline treated B cells were determined using TNFα ELISA. As shown in FIG. 4, both 1,3-dioxo-(2,6-dioxopiperidin-3-yl)-4-aminoisoindoline and 1-oxo-(2,6-dioxopiperidin-3-yl)-4-aminoisoindoline dose dependently enhance TNFα production in B cells.

6.5 Measurement of Cytokine IL-6 by Luminex

B cells were treated with 1,3-dioxo-(2,6-dioxopiperidin-3-yl)-4-aminoisoindoline at 60 μM, 6 μM, 0.6 μM, 0.06 μM, 0.006 μM and 0.0006 μM in presence of anti IgM, anti CD40 and IL-4 for 3 days. Supernatant (25 μl) was collected and incubated with 25 μl anti IL-6 beads for about 1 hour. The beads were washed three times, then incubated with 25 μl detection antibody and subsequent streptavidin-phycoerthrin for 1 hour. The beads were washed three times prior to resuspending in 100 μl Sheath Fluid. The plate was read on Bio-Plex instrument (Bio-Rad). As shown in FIG. 5, 1,3-dioxo-(2,6-dioxopiperidin-3-yl)-4-aminoisoindoline, in combination with anti IgM, anti CD40 and IL-4, enhanced IL-6 expression by immunomodulatory compound in a dose dependent manner (FIG. 5B), but alone, did not enhance the expression of IL-6 (FIG. 5A).

6.6 Morphological Changes of Activated B Cells

B cells were treated with 1,3-dioxo-(2,6-dioxopiperidin-3-yl)-4-aminoisoindoline (FIG. 6) in presence of anti IgM, anti CD40 and IL-4 for 3 days. The images were captured using phase contrast microscopy with MetaMorph software.

6.7 Cell proliferation by BrdU ELISA

The crosslinking of B cell receptor antigen ("BCR") is the primary signal for B cell activation in response to antigen, and is critical in initializing subsequent B cell activation, proliferation, and differentiation. To assess B cell activation, B cells were treated with 1,3-dioxo-(2,6-dioxopiperidin-3-yl)-4-aminoisoindoline or 1-oxo-(2,6-dioxopiperidin-3-yl)-4-aminoisoindoline in presence of stimuli for 3 days. 25 μl BrdU was added to 250 μl cell culture 24 hours before harvesting cells. B cells were dried at 60° C. after removal of labeling supernatant. 100 μl FixDenat solution was added to fix cells for 30 min at room temperature. FixDenat solution was removed by tapping plate, then 100 μl anti-BrdU-POD was added each well for 90 min, at room temperature, and the plate was washed three 3 times. 100 μl of substrate was added to plate for 10 min, then 100 μl stop solution was added. Absorbance was measured by using an ELISA microplate reader (Molecular Devices) at OD 450 nm. As shown in FIG. 7A, both immunomodulatory compounds, while having minimal effect on B cell activation alone, enhance B cell proliferation when combined with IgM that functions as cross-linking of the BCR on B cell surface, resulting in the activation of B cells.

Morphological changes also support IMiDs' costimulation of B cells to drive their proliferation. As shown in FIG. 7B, when treated by 1,3-dioxo-(2,6-dioxopiperidin-3-yl)-4-aminoisoindoline and anti-IgM, B cells formed large aggregates which were significantly different from unstimulated B cells or B cells treated with 1,3-dioxo-(2,6-dioxopiperidin-3-yl)-4-aminoisoindoline alone, or 1,3-dioxo-(2,6-dioxopiperidin-3-yl)-4-aminoisoindoline with anti-CD40 plus IL-4. Clearly, IMiDs are acting as a co-stimulus for BCR to promote B cell proliferation.

Other factors may also result in B-cell activation and proliferation. In this regard, B cell proliferation mediated by LPS and BAFF signaling was also examined. As shown in FIG. 7C, 1,3-dioxo-(2,6-dioxopiperidin-3-yl)-4-aminoisoindoline showed a similar effect to anti-IgM. LPS binds to BCR to activate B cells while BAFF triggers a unique B cell response through BAFF receptors. The modulation of BCR and BAFF cell signaling by 1,3-dioxo-(2,6-dioxopiperidin-3-yl)-4-aminoisoindoline suggests that IMiDs could potentially promote humoral immune responses, especially thymus-independent responses.

6.8 TLR 9 Expression by Facsarray

B cells were plated in 96 well plate and treated with 1,3-dioxo-(2,6-dioxopiperidin-3-yl)-4-aminoisoindoline at concentrations of 60 μM, 6 μM, 0.6 μM, 0.06 μM, 0.006 μM and 0.0006 μM in presence of stimuli for 3 days. B cells were fixed by 1% paraformaldehyde for 30 minutes, followed by permeablizing cells with 1% Triton X-100 for 30 minutes. B cells were incubated with anti human TLR 9 antibody R—PHYCOERYTHIN (PE)-conjugated anti human TLR 9 antibody for 1 hour in dark (0.5 μg/$10^6$ cells). B cells were then washed with PBS once. B cells were resuspended in 150 μl PBS containing 1% BSA and read in FACS array instrument (BD Bioscience). FIGS. 8A-8D show that an immunomodulatory compound can increase TLR expression in combination with other stimuli, particularly with IgM.

6.9 Effects on Cytokine Signaling

Effects of immunomodulatory compounds on cytokine signaling, which impact on B cell proliferation have been examined using procedures described in section 6.1.3, above. As shown in FIGS. 9A-9C, immunomodulatory compounds showed inhibitory effects on IL-4 induced cell proliferation, whereas promotional effects were seen for IL-2, IL-5, and IFN-gamma induced cell proliferation. The results are summarized in FIG. 9D.

6.9.1 Effects on IL-4 Mediated B Cell Activation

To assess whether the effects of immunomodulatory compounds on IL-4 signaling impact on IL-4 mediated B cell activation, FACS array of immediate early expression marker CD69 expression at triplicates and six doses was examined using 1,3-dioxo-(2,6dioxopiperidin-3-yl)-4-aminoisoindoline or 1-oxo-(2,6-dioxopiperidin-3-yl)-4-aminoisoindoline. As shown in FIGS. 10A and B, neither immunomodulatory compound inhibited CD69 expression in IL-4 stimulated $CD19^+$ B cells. Thus, it is clear that immunomodulatory compounds have no impact on this process.

6.9.2 IMiDs Inhibit IgE Synthesis Via Stat6 Signaling

IL-4 is a unique signal for B cells to produce IgE during the immunoglobulin class switch. To assess whether immunomodulatory compounds can regulated IgE synthesis, 1,3-dioxo-(2,6-dioxopiperidin-3-yl)-4-aminoisoindoline or 1-oxo-(2,6-dioxopiperidin-3-yl)-4-aminoisoindoline was incubated with human PBMCs in presence of CD40+IL-4 for three weeks. The data showed these compounds indeed inhibited IgE synthesis in a dose dependent manner with $IC_{50}$ around 0.1 μM-0.3 μM. (FIGS. 11A and B).

Immunomodulatory compounds also inhibited IgG1 synthesis, which is mediated by IL-4 signaling as well (FIG. 11C). IL-4 has been shown to bind the receptor to trigger STAT6 signaling to promote IgE gene transcription. Because activation of STAT6 is important in IL-4 induced IgE and $IgG_1$ class switching, whether immunomodulatory compounds could inhibit phosphorylation of STAT6 was investigated. B cells were pretreated with 1,3-dioxo-(2,6-dioxopiperidin-3-yl)-4-aminoisoindoline for 30 minutes, then stimulated with 100 ng/ml of IL-4 for 30 minutes. The activation of STAT6 was assessed by anti-phospho-STAT6 (Tyr 641). The data showed that immunomodulatory compounds can block phosphorylation of STAT6 (FIG. 11D).

In addition to the suppression of IL-4 induced proliferation, CD40+IL-4 induced HLA-DR expression was also examined. B cells were treated by 1,3-dioxo-(2,6-dioxopiperidin-3-yl)-4-aminoisoindoline with CD40L+IL-4 for 72 hours, and the cell surface expression markers CD40 and HLA-DR were measured by FACS. The data showed that B cells could be activated in response to stimulation alone, but no enhancement with immunomodulatory compound was observed (FIG. 11E). In contrast, for the B cells that were treated with BAFF, 1,3-dioxo-(2,6-dioxopiperidin-3-yl)-4-aminoisoindoline increased CD40 expression by 60% and HLA-DR expression by 86% (FIG. 11F). The data are consistent with the previous observation that immunomodulatory compounds have no effect on CD40+IL-4 signaling. Therefore, immunomodulatory compounds were shown to block CD40/IL-4/IgE signaling associated with inhibition of B cell proliferation.

6.10 Inhibition of IgE Production by Various IMiDs 6.10.1 Procedures

Treatment of PBMC: 200 μl of $1×10^6$/ml human PBMC were plated in 96 well plate, and the cells were pretreated with IMiDs at indicated concentrations (60, 6, 0.6, 0.06, 0.006, 0.0006 uM) for 30 minutes. Anti CD40 (#AHS4002, Biosource, 2 μg/ml) and IL-4 (#200-04, Pepro Tech, 40 ng/ml) were added to each well. Human PBMC in presence of IMiDs, anti CD40 and IL-4 were incubated for three weeks. Fifty microliters of supernatant was subjected to IgE ELISA.

IgE ELISA: The IgE ELISA Quantitation Kit was purchased from Bethyl Laboratories, Inc. (#E80-108). The Nunc-Immuno ELISA plate (Nalge Nunc International) was coated with 1:1000 goat anti human IgE at room temperature for 1 hour, and the plate was blocked with 1% BSA for 30 minutes. Fifty microliters of supernatant and 100 μl IgE standard were added to each well and incubated at room temperature for 2 hours. Then the plate was washed with PBS 3 times. One hundred microliters of goat anti human IgE-HRP conjugated antibody was added to each well and incubated for 60 minutes. The ELISA plate was read at OD=450 nm in ELISA plate reader.

6.10.2 Results

As shown in Table 1, below, out of 12 IMiDs tested, five showed particularly potent characteristics in inhibiting IgE synthesis. The inhibition of IgE was correlated with anti-inflammatory property of IMiDs. Table 2 shows the correlation between IgE inhibition and EC50 of IMiDs for IFN-gamma and IL-2. Since IFN-gamma is a strong antagonist of IL-4/IgE signaling, the results suggest that potential stimulation of IFN-gamma in this system might be involved in the mechanism of IgE inhibition. These results are indicative of therapeutic efficacy of IMiDs in allergic disorders.

TABLE 1

Correlation Between Inhibition of IgE and Pro-inflammatory Cytokines

| IMiD | $IC_{50}$ Ig E | $IC_{50}$ TNFα | $IC_{50}$ IL-1β | $IC_{50}$ IL-6 | $IC_{50}$ IL-12 | $IC_{50}$ MCP-1 | $IC_{50}$ MIP-1α | % IL-10 (+LPS) | % Rantes (+LPS) |
|---|---|---|---|---|---|---|---|---|---|
| 1 | + | ++ | + | + | +++ | + | + | ++ | + |
| 2 | +++ | +++ | +++ | +++ | +++ | +++ | +++ | +++ | ++ |
| 3 | +++ | +++ | +++ | +++ | +++ | ++ | ++ | +++ | ++ |

TABLE 1-continued

Correlation Between Inhibition of IgE and Pro-inflammatory Cytokines

| IMiD | IC$_{50}$ IgE | IC$_{50}$ TNFα | IC$_{50}$ IL-1β | IC$_{50}$ IL-6 | IC$_{50}$ IL-12 | IC$_{50}$ MCP-1 | IC$_{50}$ MIP-1α | % IL-10 (+LPS) | % Rantes (+LPS) |
|---|---|---|---|---|---|---|---|---|---|
| 4 | NT | +++ | +++ | +++ | +++ | ++ | +++ | +++ | ++ |
| 5 | +++ | +++ | +++ | +++ | +++ | +++ | +++ | +++ | ++ |
| 6 | ++ | + | + | + | ++ | + | + | + | + |
| 7 | +++ | +++ | +++ | +++ | +++ | +++ | +++ | +++ | ++ |
| 8 | ++ | +++ | +++ | ++ | +++ | + | + | +++ | ++ |
| 9 | +++ | +++ | +++ | +++ | +++ | +++ | +++ | +++ | ++ |
| 10 | + | + | + | + | + | + | + | + | + |
| 11 | + | ++ | ++ | + | ++ | + | + | ++ | ++ |
| 12 | ++ | ++ | + | + | +++ | + | + | ++ | ++ |

TABLE 2

Correlation Between IgE Inhibition and IFN-γ/IL-2 Stimulation

| IMiD | IC$_{50}$ IgE | EC$_{50}$ IFN-γ | EC$_{50}$ IL-2 |
|---|---|---|---|
| 1 | + | + | + |
| 2 | +++ | +++ | +++ |
| 3 | +++ | +++ | +++ |
| 4 | NT | +++ | +++ |
| 5 | +++ | +++ | +++ |
| 6 | ++ | ++ | + |
| 7 | +++ | + | ++ |
| 8 | ++ | +++ | ++ |
| 9 | +++ | +++ | +++ |
| 10 | + | + | + |
| 11 | + | + | ++ |
| 12 | ++ | ++ | + |

All of the references cited herein are incorporated by reference in their entirety. While the invention has been described with respect to the particular embodiments, it will be apparent to those skilled in the art that various changes and modifications may be made without departing from the spirit and scope of the invention as recited by the appended claims.

The embodiments of the invention described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A method of treating or managing an immunodeficiency disease or disorder, which comprises administering to a patient in need of such treatment or management a therapeutically effective amount of an immunomodulatory compound of formula (I),

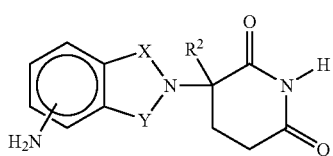

or a pharmaceutically acceptable salt, solvate, or stereoisomer thereof,
wherein one of X and Y is C=O, the other of X and Y is C=O or CH2, and R2 is hydrogen or lower alkyl; and
wherein the immunodeficiency disease or disorder is adenosine deaminase deficiency, antibody deficiency with normal or elevated Igs, ataxia-telangiectasia, bare lymphocyte syndrome, common variable immunodeficiency, Ig deficiency with hyper-IgM, Ig heavy chain deletions, IgA deficiency, immunodeficiency with thymoma, reticular dysgenesis, Nezelof syndrome, selective IgG subclass deficiency, transient hypogammaglobulinemia of infancy, Wiskott-Aldrich syndrome, X-linked agammaglobulinemia, or X-linked severe combined immunodeficiency.

2. The method of claim 1, wherein the immunodeficiency disease or disorder is primary immunodeficiency or secondary immunodeficiency.

3. The method of claim 2, wherein the immunodeficiency disease or disorder is primary immunodeficiency.

4. The method of claim 1, wherein the immunodeficiency disease or disorder is X-linked agammaglobulinemia.

5. The method of claim 1, wherein the immunomodulatory compound is 4-(amino)-2-(2,6-dioxo(3-piperidyl))-isoindoline-1,3-dione.

6. The method of claim 5, wherein the immunomodulatory compound is enantiomerically pure.

7. The method of claim 1, wherein the immunomodulatory compound is 3-(4-amino-1-oxo-1,3-dihydro-isoindol-2-yl)-piperidine-2,6-dione.

8. The method of claim 7, wherein the immunomodulatory compound is enantiomerically pure.

9. The method of claim 1, further comprising administering an anti-CD40 antibody to said patient.

10. The method of claim 1, further comprising administering CD40L to said patient.

* * * * *